US012011227B2

(12) United States Patent
Grupp, Jr. et al.

(10) Patent No.: US 12,011,227 B2
(45) Date of Patent: Jun. 18, 2024

(54) METHODS AND SYSTEMS FOR DETERMINING ALIGNMENT PARAMETERS OF A SURGICAL TARGET, SUCH AS A SPINE

(71) Applicant: Proprio, Inc., Seattle, WA (US)

(72) Inventors: Robert Bruce Grupp, Jr., Edgewood, WA (US); David Lee Fiorella, Seattle, WA (US); Thomas A. Carls, Memphis, TN (US); Samuel R. Browd, Mercer Island, WA (US); Adam Gabriel Jones, Seattle, WA (US); James Andrew Youngquist, Seattle, WA (US); Richard Earl Simpkinson, Issaquah, WA (US)

(73) Assignee: PROPRIO, INC., Seattle, WA (US)

( * ) Notice: Subject to any disclaimer, the term of this patent is extended or adjusted under 35 U.S.C. 154(b) by 0 days.

(21) Appl. No.: 17/735,945

(22) Filed: May 3, 2022

(65) Prior Publication Data
US 2023/0355309 A1    Nov. 9, 2023

(51) Int. Cl.
*G06K 9/00* (2022.01)
*A61B 17/88* (2006.01)
(Continued)

(52) U.S. Cl.
CPC .......... *A61B 34/10* (2016.02); *A61B 17/8863* (2013.01); *G16H 50/50* (2018.01);
(Continued)

(58) Field of Classification Search
CPC ............... A61B 34/10; A61B 17/8863; A61B 2034/2055; A61B 2034/2051;
(Continued)

(56) References Cited

U.S. PATENT DOCUMENTS 8,010,177 B2    8/2011    Csavoy et al.
9,119,670 B2    9/2015    Yang et al.
(Continued)

FOREIGN PATENT DOCUMENTS

| CN | 110381874 A | * | 10/2019 | ............ A61B 34/10 |
| WO | 2011078933 A1 | | 6/2011 | |
| WO | 2015074158 A1 | | 5/2015 | |

OTHER PUBLICATIONS

U.S. Appl. No. 16/457,780, titled "Synthesizing an Image From a Virtual Perspective Using Pixels From a Physical Imager Array Weighted Based On Depth Error Sensitivity," and filed Jun. 28, 2019.

(Continued)

*Primary Examiner* — Shervin K Nakhjavan
(74) *Attorney, Agent, or Firm* — Perkins Coie LLP

(57) ABSTRACT

Methods and systems for intraoperatively determining alignment parameters of a spine during a spinal surgical procedure are disclosed herein. In some embodiments, a method of intraoperatively determining an alignment parameter of a spine during a surgical procedure includes receiving initial image data of the spine including multiple vertebrae and identifying a geometric feature associated with each vertebra in the initial image data. The geometric features each have a pose in the initial image data and characterize a three-dimensional (3D) shape of the associated vertebra. The method further comprises receiving intraoperative image data of the spine and registering the initial image data to the intraoperative image data. The method can then update the pose of each geometric feature based on the registration and the intraoperative image data, and determine the alignment parameter based on the updated poses of the geometric features associated with two or more of the vertebrae.

19 Claims, 22 Drawing Sheets

(51) Int. Cl.
*A61B 34/10* (2016.01)
*G16H 50/50* (2018.01)
*A61B 34/20* (2016.01)

(52) U.S. Cl.
CPC ............... *A61B 2034/2055* (2016.02); *G06T 2207/30012* (2013.01)

(58) Field of Classification Search
CPC .... A61B 2034/2057; A61B 2034/2065; A61B 2034/2068; A61B 2090/365; A61B 2090/367; A61B 2090/371; A61B 2090/372; A61B 2090/502; A61B 34/20; G16H 50/50; G16H 20/40; G16H 30/40; G06T 2207/30012

See application file for complete search history.

(56) References Cited

U.S. PATENT DOCUMENTS

| | | | |
|---|---|---|---|
| 9,968,408 | B1 | 5/2018 | Casey et al. |
| 10,682,185 | B2 * | 6/2020 | Hladio ................. A61B 46/10 |
| 10,709,509 | B2 | 7/2020 | Scholl et al. |
| 10,792,110 | B2 * | 10/2020 | Leung ..................... G06T 7/74 |
| 10,949,986 | B1 | 3/2021 | Colmenares et al. |
| 11,224,483 | B2 * | 1/2022 | Steinberg ............... A61B 90/36 |
| 11,276,187 | B2 * | 3/2022 | Ben-Yishai ............ G06T 7/337 |
| 11,295,460 | B1 | 4/2022 | Aghdasi et al. |
| 11,406,471 | B1 * | 8/2022 | Paulsen ................. A61B 90/361 |
| 11,452,570 | B2 * | 9/2022 | Tolkowsky .......... A61B 6/5241 |
| 2010/0054525 | A1 | 3/2010 | Gong et al. |
| 2013/0060146 | A1 * | 3/2013 | Yang ..................... G01B 11/25 600/476 |
| 2016/0019188 | A1 | 1/2016 | Zulch et al. |
| 2018/0150960 | A1 * | 5/2018 | Derda ................... A61B 6/5223 |
| 2018/0301213 | A1 * | 10/2018 | Zehavi ..................... G06T 7/70 |
| 2019/0076195 | A1 * | 3/2019 | Shalayev ............... A61B 34/10 |
| 2019/0209080 | A1 | 7/2019 | Gullotti et al. |
| 2019/0321116 | A1 * | 10/2019 | Kerdok .................. A61B 34/76 |
| 2020/0053335 | A1 * | 2/2020 | Casas ................. G02B 27/0172 |
| 2020/0105065 | A1 | 4/2020 | Youngquist et al. |
| 2020/0221974 | A1 * | 7/2020 | Singh .................... A61B 5/0024 |
| 2020/0352651 | A1 * | 11/2020 | Junio ..................... A61B 34/10 |
| 2020/0405399 | A1 * | 12/2020 | Steinberg ............... A61B 6/466 |
| 2021/0077047 | A1 * | 3/2021 | Tolkowsky ............ A61B 90/39 |
| 2021/0121237 | A1 * | 4/2021 | Fanson .................. A61B 34/20 |
| 2021/0192763 | A1 * | 6/2021 | Liu ........................ A61B 34/20 |
| 2021/0244485 | A1 * | 8/2021 | Coiseur ................ A61B 90/361 |
| 2021/0330250 | A1 * | 10/2021 | Redmond .............. A61B 90/06 |
| 2022/0013211 | A1 * | 1/2022 | Steinberg ............... G16H 30/20 |
| 2022/0110698 | A1 * | 4/2022 | Tolkowsky ............ A61B 34/30 |
| 2022/0160322 | A1 * | 5/2022 | Homan .................. A61B 6/469 |
| 2022/0183760 | A1 * | 6/2022 | Fouts .................... G16H 50/20 |
| 2022/0198665 | A1 * | 6/2022 | Mahendra .............. A61B 34/10 |

OTHER PUBLICATIONS

U.S. Appl. No. 16/749,963, titled "Aligning Preoperative Scan Images To Real-Time Operative Images for a Mediated-Reality View of a Surgical Site," filed Jan. 22, 2020.

U.S. Appl. No. 17/140,885, titled "Methods and Systems for Registering Preoperative Image Data To Intraoperative Image Data of a Scene, Such as a Surgical Scene," and filed Jan. 4, 2021.

International Search Report and Written Opinion from PCT Application No. PCT/US2023/066514 dated Jul. 7, 2023.

* cited by examiner

```
                      ┌─ 534
        ╭─────────────────────────────────╮
        │ Register the initial image data │
        │ of the spine to the             │
        │ intraoperative image data       │
        ╰─────────────────────────────────╯
                        │
                        ▼          ┌─ 1061
        ┌─────────────────────────────────────────┐
        │ Receive a three-dimensional (3D) model  │
        │ of a surgical device configured to be   │
        │ secured to a vertebra of the spine      │
        └─────────────────────────────────────────┘
                        │
                        ▼          ┌─ 1062
        ┌─────────────────────────────────────────┐
        │ Determine a spatial relationship        │
        │ between the surgical device and the     │
        │ vertebra it is secured to               │
        └─────────────────────────────────────────┘
                        │
                        ▼          ┌─ 1063
        ┌─────────────────────────────────────────┐
        │ Receive intraoperative image data of    │
        │ the surgical device                     │
        └─────────────────────────────────────────┘
                        │
                        ▼          ┌─ 1064
        ┌─────────────────────────────────────────┐
        │ Register the initial image data of the  │
        │ spine to the intraoperative image data  │
        │ based on the spatial relationship       │
        └─────────────────────────────────────────┘
```

*FIG. 10*

METHODS AND SYSTEMS FOR DETERMINING ALIGNMENT PARAMETERS OF A SURGICAL TARGET, SUCH AS A SPINE

TECHNICAL FIELD

The present technology generally relates to methods and systems for intraoperatively determining alignment parameters of a spine of a patient undergoing a spinal surgical procedure.

BACKGROUND

Spinal deformities involve pathologic curvatures of the spine and can occur naturally, or as a result of disease or damage to the spine. Spinal deformities may occur along the coronal, sagittal, and/or axial planes, and can include scoliosis, hyper-lordosis, hypo-lordosis, hyper-kyphosis, hypo-kyphosis, and the like. In some instances, spinal deformities require surgical correction. Spinal surgery can be done by exposing a portion of the spine and/or via minimally invasive techniques that physically manipulate the bones of the spine into a corrected configuration which is temporarily held in place by surgical hardware (e.g., pedicle screws, rod and tower devices, interbody devices) until bone growth creates a permanent fixation.

Existing navigation systems for spine deformity surgery are limited to guiding the placement of hardware. Accordingly, surgeons must rely upon manual interpretation of either (i) the exposed physical anatomy or (ii) intraoperatively acquired two-dimensional (2D) or three-dimensional (3D) radiographs (e.g., X-rays) or computed tomography (CT) images to assess the progress of the surgery, such as corrections to the spine deformity. Subjective mental assessment of the exposed physical anatomy and the operative field by the surgeon is challenging and potentially imprecise/non-repeatable, introducing more of an "art" to the surgery. Although interpretation of existing 2D or 3D X-ray imaging may reduce the degree of subjectiveness in correction assessment, the image acquisition process interferes with the surgical workflow and exposes both the patient and the surgical team to potentially harmful amounts of ionizing radiation.

BRIEF DESCRIPTION OF THE DRAWINGS

Many aspects of the present disclosure can be better understood with reference to the following drawings. The components in the drawings are not necessarily to scale. Instead, emphasis is placed on clearly illustrating the principles of the present disclosure.

FIG. 10 is a flow diagram of a process or method for registering initial image data to intraoperative image data based on one or more surgical devices in accordance with embodiments of the present technology.

DETAILED DESCRIPTION

Figure 1:
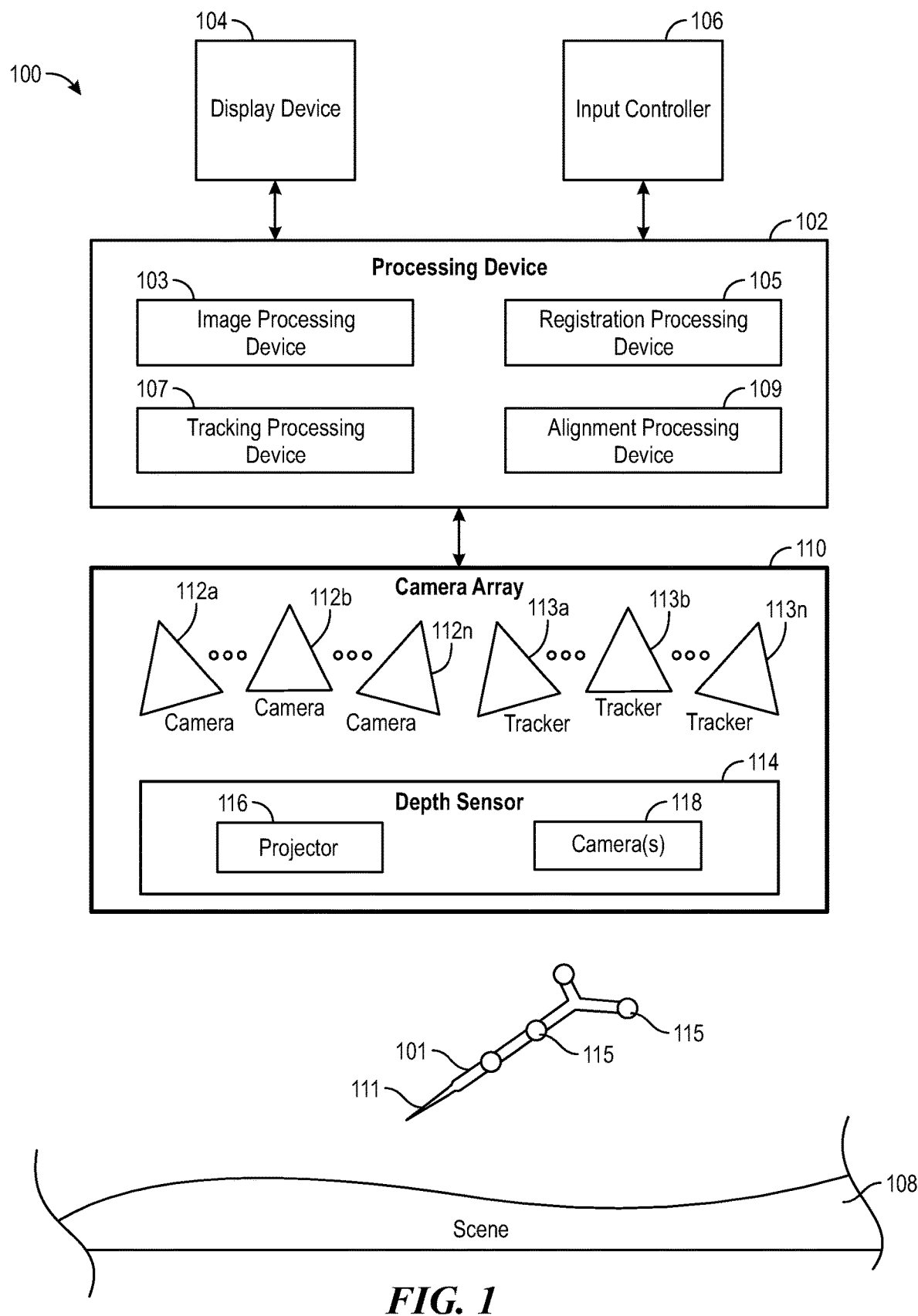
FIG. 1 is a schematic view of an imaging system in accordance with embodiments of the present technology.

Aspects of the present technology are directed generally to methods and systems for intraoperatively determining alignment parameters of a spine of a patient during, for example, a spinal surgical procedure. In several of the embodiments described below, a method of intraoperatively determining an alignment parameter of a spine during a surgical procedure on the spine includes receiving initial image data of the spine (e.g., preoperative computed tomography (CT) data) including multiple vertebrae and identifying a geometric feature associated with each vertebra in the initial image data. The geometric features each have a pose in the initial image data and characterize a three-dimensional (3D) shape of the associated vertebra. The method further comprises receiving intraoperative image data of the spine from, for example, a camera array positioned over the surgical scene. The method further comprises registering the initial image data to the intraoperative image data, and updating the pose of each geometric feature based on the registration and the intraoperative image data. The method then determines the alignment parameter of the spine based on the updated poses of the geometric features associated with two or more of the vertebrae.

In some embodiments, the alignment parameter characterizes a curvature of the spine, such as a Cobb or other angle. In some aspects of the present technology, the method can determine the alignment parameter continuously in substantially real-time such that that alignment parameter continuously reflects the true physical alignment of the spine during the surgical procedure. A surgeon or other user can use the determined spinal alignment parameter to track their progress through the surgical procedure and/or to confirm the effectiveness thereof.

Specific details of several embodiments of the present technology are described herein with reference to FIGS. 1-12. The present technology, however, can be practiced without some of these specific details. In some instances, well-known structures and techniques often associated with camera arrays, light field cameras, image reconstruction, registration processes, spinal analysis, spinal deformities, and the like have not been shown in detail so as not to obscure the present technology.

The terminology used in the description presented below is intended to be interpreted in its broadest reasonable manner, even though it is being used in conjunction with a detailed description of certain specific embodiments of the disclosure. Certain terms can even be emphasized below; however, any terminology intended to be interpreted in any restricted manner will be overtly and specifically defined as such in this Detailed Description section.

The accompanying Figures depict embodiments of the present technology and are not intended to be limiting of its scope. Depicted elements are not necessarily drawn to scale, and various elements can be arbitrarily enlarged to improve legibility. Component details can be abstracted in the figures to exclude details as such details are unnecessary for a complete understanding of how to make and use the present technology. Many of the details, dimensions, angles, and other features shown in the Figures are merely illustrative of particular embodiments of the disclosure. Accordingly, other embodiments can have other dimensions, angles, and features without departing from the spirit or scope of the present technology.

The headings provided herein are for convenience only and should not be construed as limiting the subject matter disclosed. To the extent any materials incorporated herein by reference conflict with the present disclosure, the present disclosure controls.

I. SELECTED EMBODIMENTS OF IMAGING SYSTEMS

FIG. 1 is a schematic view of an imaging system 100 ("system 100") in accordance with embodiments of the present technology. In some embodiments, the system 100 can be a synthetic augmented reality system, a virtual-reality imaging system, an augmented-reality imaging system, a mediated-reality imaging system, and/or a non-immersive computational imaging system. In the illustrated embodiment, the system 100 includes a processing device 102 that is communicatively coupled to one or more display devices 104, one or more input controllers 106, and a camera array 110. In other embodiments, the system 100 can comprise additional, fewer, or different components. In some embodiments, the system 100 includes some features that are generally similar or identical to those of the mediated-reality imaging systems disclosed in (i) U.S. patent application Ser. No. 16/586,375, titled "CAMERA ARRAY FOR A MEDIATED-REALITY SYSTEM," and filed Sep. 27, 2019 and/or (ii) U.S. patent application Ser. No. 15/930,305, titled "METHODS AND SYSTEMS FOR IMAGING A SCENE, SUCH AS A MEDICAL SCENE, AND TRACKING OBJECTS WITHIN THE SCENE," and filed May 12, 2020, each of which is incorporated herein by reference in its entirety.

In the illustrated embodiment, the camera array 110 includes a plurality of cameras 112 (identified individually as cameras 112a-112n; which can also be referred to as first cameras) that can each capture images of a scene 108 (e.g., first image data) from a different perspective. The scene 108 can include for example, a patient undergoing surgery (e.g., spinal surgery) and/or another medical procedure. In other embodiments, the scene 108 can be another type of scene. The camera array 110 can further include dedicated object tracking hardware 113 (e.g., including individually identified trackers 113a-113n) that captures positional data of one more objects, such as an instrument 101 (e.g., a surgical instrument or tool) having a tip 111, to track the movement and/or orientation of the objects through/in the scene 108. In some embodiments, the cameras 112 and the trackers 113 are positioned at fixed locations and orientations (e.g., poses) relative to one another. For example, the cameras 112 and the trackers 113 can be structurally secured by/to a mounting structure (e.g., a frame) at predefined fixed locations and orientations. In some embodiments, the cameras 112 are positioned such that neighboring cameras 112 share overlapping views of the scene 108. In general, the position of the cameras 112 can be selected to maximize clear and accurate capture of all or a selected portion of the scene 108. Likewise, the trackers 113 can be positioned such that neighboring trackers 113 share overlapping views of the scene 108. Therefore, all or a subset of the cameras 112 and the trackers 113 can have different extrinsic parameters, such as position and orientation.

In some embodiments, the cameras 112 in the camera array 110 are synchronized to capture images of the scene 108 simultaneously (within a threshold temporal error). In some embodiments, all or a subset of the cameras 112 are light field/plenoptic/RGB cameras that capture information about the light field emanating from the scene 108 (e.g., information about the intensity of light rays in the scene 108 and also information about a direction the light rays are traveling through space). Therefore, in some embodiments the images captured by the cameras 112 encode depth information representing a surface geometry of the scene 108. In some embodiments, the cameras 112 are substantially identical. In other embodiments, the cameras 112 include multiple cameras of different types. For example, different subsets of the cameras 112 can have different intrinsic parameters such as focal length, sensor type, optical components, and the like. The cameras 112 can have charge-coupled device (CCD) and/or complementary metal-oxide semiconductor (CMOS) image sensors and associated optics. Such optics can include a variety of configurations including lensed or bare individual image sensors in combination with larger macro lenses, micro-lens arrays, prisms, and/or negative lenses. For example, the cameras 112 can be separate light field cameras each having their own image sensors and optics. In other embodiments, some or all of the cameras 112 can comprise separate microlenslets (e.g., lenslets, lenses, microlenses) of a microlens array (MLA) that share a common image sensor.

In some embodiments, the trackers 113 are imaging devices, such as infrared (IR) cameras that can capture images of the scene 108 from a different perspective compared to other ones of the trackers 113. Accordingly, the trackers 113 and the cameras 112 can have different spectral sensitives (e.g., infrared vs. visible wavelength). In some embodiments, the trackers 113 capture image data of a plurality of optical markers (e.g., fiducial markers, marker balls) in the scene 108, such as markers 115 coupled to the instrument 101.

In the illustrated embodiment, the camera array 110 further includes a depth sensor 114. In some embodiments, the depth sensor 114 includes (i) one or more projectors 116 that project a structured light pattern onto/into the scene 108 and (ii) one or more depth cameras 118 (which can also be referred to as second cameras) that capture second image data of the scene 108 including the structured light projected onto the scene 108 by the projector 116. The projector 116 and the depth cameras 118 can operate in the same wavelength and, in some embodiments, can operate in a wavelength different than the cameras 112. For example, the cameras 112 can capture the first image data in the visible spectrum, while the depth cameras 118 capture the second image data in the infrared spectrum. In some embodiments, the depth cameras 118 have a resolution that is less than a resolution of the cameras 112. For example, the depth cameras 118 can have a resolution that is less than 70%, 60%, 50%, 40%, 30%, or 20% of the resolution of the cameras 112. In other embodiments, the depth sensor 114 can include other types of dedicated depth detection hardware (e.g., a LiDAR detector) for determining the surface geometry of the scene 108. In other embodiments, the camera array 110 can omit the projector 116 and/or the depth cameras 118.

In the illustrated embodiment, the processing device 102 includes an image processing device 103 (e.g., an image processor, an image processing module, an image processing unit), a registration processing device 105 (e.g., a registration processor, a registration processing module, a registration processing unit), a tracking processing device 107 (e.g., a tracking processor, a tracking processing module, a tracking processing unit), and an alignment processing device 109. The image processing device 103 can (i) receive the first image data captured by the cameras 112 (e.g., light field images, hyperspectral images, light field image data, RGB images) and depth information from the depth sensor 114 (e.g., the second image data captured by the depth cameras 118), and (ii) process the image data and depth information to synthesize (e.g., generate, reconstruct, render) a three-dimensional (3D) output image of the scene 108 corresponding to a virtual camera perspective. The output image can correspond to an approximation of an image of the scene 108 that would be captured by a camera placed at an arbitrary position and orientation corresponding to the virtual camera perspective. In some embodiments, the image processing device 103 can further receive and/or store calibration data for the cameras 112 and/or the depth cameras 118 and synthesize the output image based on the image data, the depth information, and/or the calibration data. More specifically, the depth information and the calibration data can be used/combined with the images from the cameras 112 to synthesize the output image as a 3D (or stereoscopic 2D) rendering of the scene 108 as viewed from the virtual camera perspective. In some embodiments, the image processing device 103 can synthesize the output image using any of the methods disclosed in U.S. patent application Ser. No. 16/457,780, titled "SYNTHESIZING AN IMAGE FROM A VIRTUAL PERSPECTIVE USING PIXELS FROM A PHYSICAL IMAGER ARRAY WEIGHTED BASED ON DEPTH ERROR SENSITIVITY," and filed Jun. 28, 2019, which is incorporated herein by reference in its entirety. In other embodiments, the image processing device 103 can generate the virtual camera perspective based only on the images captured by the cameras 112—without utilizing depth information from the depth sensor 114. For example, the image processing device 103 can generate the virtual camera perspective by interpolating between the different images captured by one or more of the cameras 112.

The image processing device 103 can synthesize the output image from images captured by a subset (e.g., two or more) of the cameras 112 in the camera array 110, and does not necessarily utilize images from all of the cameras 112. For example, for a given virtual camera perspective, the processing device 102 can select a stereoscopic pair of images from two of the cameras 112. In some embodiments, such a stereoscopic pair can be selected to be positioned and oriented to most closely match the virtual camera perspective. In some embodiments, the image processing device 103 (and/or the depth sensor 114) estimates a depth for each surface point of the scene 108 relative to a common origin to generate a point cloud and/or a 3D mesh that represents the surface geometry of the scene 108. Such a representation of the surface geometry can be referred to as a depth map, an N35 surface, a depth surface, and/or the like. In some embodiments, the depth cameras 118 of the depth sensor 114 detect the structured light projected onto the scene 108 by the projector 116 to estimate depth information of the scene 108. In some embodiments, the image processing device 103 estimates depth from multiview image data from the cameras 112 using techniques such as light field correspondence, stereo block matching, photometric symmetry, correspondence, defocus, block matching, texture-assisted block matching, structured light, and the like, with or without utilizing information collected by the depth sensor 114. In other embodiments, depth may be acquired by a specialized set of the cameras 112 performing the aforementioned methods in another wavelength.

In some embodiments, the registration processing device 105 receives and/or stores previously-captured or initial image data, such as image data of a three-dimensional volume of a patient (3D image data). The image data can include, for example, computerized tomography (CT) scan data, magnetic resonance imaging (MM) scan data, ultrasound images, fluoroscope images, and/or other medical or other image data. The registration processing device 105 can register the initial image data to the real-time images captured by the cameras 112 and/or the depth sensor 114 by, for example, determining one or more transforms/transformations/mappings between the two. The processing device 102 (e.g., the image processing device 103) can then apply the one or more transforms to the initial image data such that the initial image data can be aligned with (e.g., overlaid on) the output image of the scene 108 in real-time or near real-time on a frame-by-frame basis, even as the virtual perspective changes. That is, the image processing device 103 can fuse the initial image data with the real-time output image of the scene 108 to present a mediated-reality view that enables, for example, a surgeon to simultaneously view a surgical site in the scene 108 and the underlying 3D anatomy of a patient undergoing an operation. In some embodiments, the registration processing device 105 can register the previously-captured image data to the real-time images using any of the methods disclosed in U.S. patent application Ser. No. 17/140,885, titled "METHODS AND SYSTEMS FOR REGISTERING PREOPERATIVE IMAGE DATA TO INTRAOPERATIVE IMAGE DATA OF A SCENE, SUCH AS A SURGICAL SCENE," and filed Jan. 4, 2021.

In some embodiments, the tracking processing device 107 processes positional data captured by the trackers 113 to track objects (e.g., the instrument 101) within the vicinity of the scene 108. For example, the tracking processing device 107 can determine the position of the markers 115 in the 2D images captured by two or more of the trackers 113, and can compute the 3D position of the markers 115 via triangulation of the 2D positional data. More specifically, in some embodiments the trackers 113 include dedicated processing hardware for determining positional data from captured images, such as a centroid of the markers 115 in the captured images. The trackers 113 can then transmit the positional data to the tracking processing device 107 for determining the 3D position of the markers 115. In other embodiments, the tracking processing device 107 can receive the raw image data from the trackers 113. In a surgical application, for example, the tracked object can comprise a surgical instrument, an implant, a hand or arm of a physician or assistant, and/or another object having the markers 115 mounted thereto. In some embodiments, the processing device 102 can recognize the tracked object as being separate from the scene 108, and can apply a visual effect to the 3D output image to distinguish the tracked object by, for example, highlighting the object, labeling the object, and/or applying a transparency to the object.

In some embodiments, the alignment processing device 109 determines (e.g., measures, calculates, computes) various alignment parameters (e.g., geometric parameters) for a surgical procedure, such as one or more angles, areas, volumes, distances, and/or the like. For example, for a spinal surgical procedure, the alignment processing device 109 can determine at least one of a Cobb angle (primary, secondary, and/or tertiary), lumbar lordosis measurement, thoracic kyphosis measurement, cervical lordosis measurement, sagittal vertical axis, pelvic tilt, pelvic angle, sacral slope, pelvic incidence, vertebral rotation angle, segmental lordosis/kyphosis measurement, anterior disc height, posterior disc height, foraminal height, foraminal area, disc volume, spondylolisthesis grading (e.g., in millimeter measurements and/or by Grade I, II, III, IV, and V), vertebral body height measurements (anterior, posterior, left, and/or right), C7 plumbline (C7PL), center sacral vertical line (CSVL), lateral olisthesis grading, sagittal vertical axis (SVA), T1 tilt, T1 pelvic angle, L1 tilt, L1 pelvic angle, etc., of the spine. As described in detail below with reference to FIGS. 4-12, the alignment processing device 109 can determine the alignment parameters of the spine in real-time or near real-time (e.g., substantially real-time) based on (i) initial image data of the spine, (ii) intraoperative image data of the spine captured by the camera array 110, and (iii) the registration between the initial image data and the intraoperative image data of the spine. Additionally, the system 100 can compute formulas and/or scores based on the alignment parameters, such as a global alignment and proportion (GAP) score.

In some embodiments, functions attributed to the processing device 102, the image processing device 103, the registration processing device 105, the tracking processing device 107, and/or the alignment processing device 109 can be practically implemented by two or more physical devices. For example, in some embodiments a synchronization controller (not shown) controls images displayed by the projector 116 and sends synchronization signals to the cameras 112 to ensure synchronization between the cameras 112 and the projector 116 to enable fast, multi-frame, multicamera structured light scans. Additionally, such a synchronization controller can operate as a parameter server that stores hardware specific configurations such as parameters of the structured light scan, camera settings, and camera calibration data specific to the camera configuration of the camera array 110. The synchronization controller can be implemented in a separate physical device from a display controller that controls the display device 104, or the devices can be integrated together.

The processing device 102 can comprise a processor and a non-transitory computer-readable storage medium that stores instructions that when executed by the processor, carry out the functions attributed to the processing device 102 as described herein. Although not required, aspects and embodiments of the present technology can be described in the general context of computer-executable instructions, such as routines executed by a general-purpose computer, e.g., a server or personal computer. Those skilled in the relevant art will appreciate that the present technology can be practiced with other computer system configurations, including Internet appliances, hand-held devices, wearable computers, cellular or mobile phones, multi-processor systems, microprocessor-based or programmable consumer electronics, set-top boxes, network PCs, mini-computers, mainframe computers and the like. The present technology can be embodied in a special purpose computer or data processor that is specifically programmed, configured or constructed to perform one or more of the computer-executable instructions explained in detail below. Indeed, the term "computer" (and like terms), as used generally herein, refers to any of the above devices, as well as any data processor or any device capable of communicating with a network, including consumer electronic goods such as game devices, cameras, or other electronic devices having a processor and other components, e.g., network communication circuitry.

The present technology can also be practiced in distributed computing environments, where tasks or modules are performed by remote processing devices, which are linked through a communications network, such as a Local Area Network ("LAN"), Wide Area Network ("WAN"), or the Internet. In a distributed computing environment, program modules or sub-routines can be located in both local and remote memory storage devices. Aspects of the present technology described below can be stored or distributed on computer-readable media, including magnetic and optically readable and removable computer discs, stored as in chips (e.g., EEPROM or flash memory chips). Alternatively, aspects of the present technology can be distributed electronically over the Internet or over other networks (including wireless networks). Those skilled in the relevant art will recognize that portions of the present technology can reside on a server computer, while corresponding portions reside on a client computer. Data structures and transmission of data particular to aspects of the present technology are also encompassed within the scope of the present technology.

The virtual camera perspective is controlled by an input controller 106 that can update the virtual camera perspective based on user driven changes to the camera's position and rotation. The output images corresponding to the virtual camera perspective can be outputted to the display device 104. In some embodiments, the image processing device 103 can vary the perspective, the depth of field (e.g., aperture), the focus plane, and/or another parameter of the virtual camera (e.g., based on an input from the input controller) to generate different 3D output images without physically moving the camera array 110. The display device 104 can receive output images (e.g., the synthesized 3D rendering of the scene 108) and display the output images for viewing by one or more viewers. In some embodiments, the processing device 102 receives and processes inputs from the input controller 106 and processes the captured images from the camera array 110 to generate output images corresponding to the virtual perspective in substantially real-time or near real-time as perceived by a viewer of the display device 104 (e.g., at least as fast as the frame rate of the camera array 110).

Additionally, the display device 104 can display a graphical representation on/in the image of the virtual perspective of any (i) tracked objects within the scene 108 (e.g., a surgical instrument) and/or (ii) registered or unregistered initial image data. That is, for example, the system 100 (e.g., via the display device 104) can blend augmented data into the scene 108 by overlaying and aligning information on top of "passthrough" images of the scene 108 captured by the cameras 112. Moreover, the system 100 can create a mediated-reality experience where the scene 108 is reconstructed using light field image date of the scene 108 captured by the cameras 112, and where instruments are virtually represented in the reconstructed scene via information from the trackers 113. Additionally or alternatively, the system 100 can remove the original scene 108 and completely replace it with a registered and representative arrangement of the initially captured image data, thereby removing information in the scene 108 that is not pertinent to a user's task.

The display device 104 can comprise, for example, a head-mounted display device, a monitor, a computer display, and/or another display device. In some embodiments, the input controller 106 and the display device 104 are integrated into a head-mounted display device and the input controller 106 comprises a motion sensor that detects position and orientation of the head-mounted display device. In some embodiments, the system 100 can further include a separate tracking system (not shown), such as an optical tracking system, for tracking the display device 104, the instrument 101, and/or other components within the scene 108. Such a tracking system can detect a position of the head-mounted display device 104 and input the position to the input controller 106. The virtual camera perspective can then be derived to correspond to the position and orientation of the head-mounted display device 104 in the same reference frame and at the calculated depth (e.g., as calculated by the depth sensor 114) such that the virtual perspective corresponds to a perspective that would be seen by a viewer wearing the head-mounted display device 104. Thus, in such embodiments the head-mounted display device 104 can provide a real-time rendering of the scene 108 as it would be seen by an observer without the head-mounted display device 104. Alternatively, the input controller 106 can comprise a user-controlled control device (e.g., a mouse, pointing device, handheld controller, gesture recognition controller) that enables a viewer to manually control the virtual perspective displayed by the display device 104.

Figure 2:
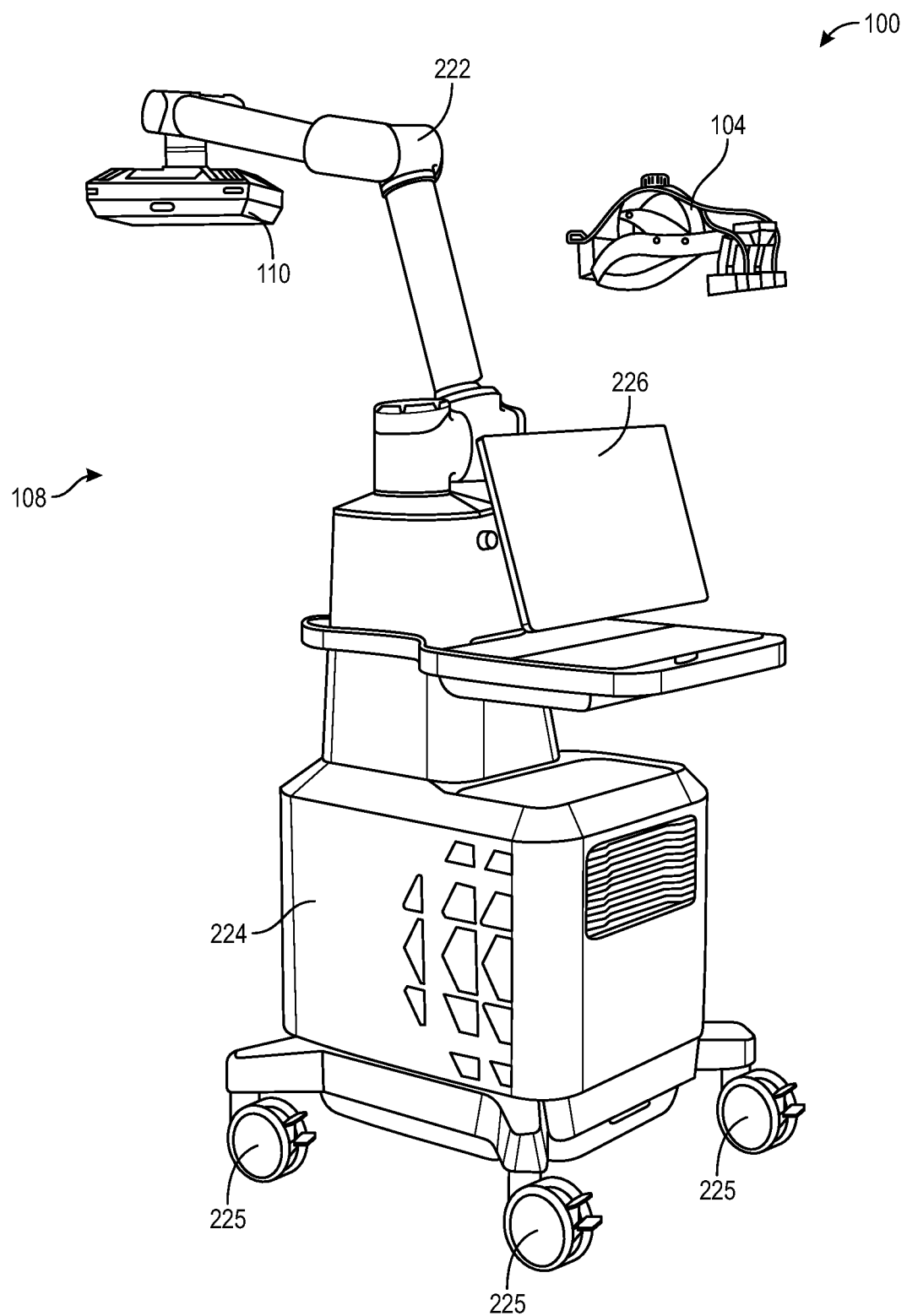
FIG. 2 is a perspective view of a surgical environment employing the imaging system of FIG. 1 for a surgical application in accordance with embodiments of the present technology.

FIG. 2 is a perspective view of a surgical environment employing the system 100 for a surgical application in accordance with embodiments of the present technology. In the illustrated embodiment, the camera array 110 is positioned over the scene 108 (e.g., a surgical site) and supported/positioned via a movable arm 222 that is operably coupled to a workstation 224. In some embodiments, the arm 222 is manually movable to position the camera array 110 while, in other embodiments, the arm 222 is robotically controlled in response to the input controller 106 (FIG. 1) and/or another controller. In the illustrated embodiment, the workstation 224 is mounted on wheels or casters 225 that allow the system 100 to be rolled. In some embodiments, the system 100 can be rolled on the casters 225 and/or the arm 222 can be moved to scan a region of the scene 108, such as a portion of a patient's spine.

In the illustrated embodiment, the display device 104 is a head-mounted display device (e.g., a virtual reality headset, augmented reality headset). The workstation 224 can include a computer to control various functions of the processing device 102, the display device 104, the input controller 106, the camera array 110, and/or other components of the system 100 shown in FIG. 1. Accordingly, in some embodiments the processing device 102 and the input controller 106 are each integrated in the workstation 224. In some embodiments, the workstation 224 includes a secondary display 226 that can display a user interface for performing various configuration functions, a mirrored image of the display on the display device 104, and/or other useful visual images/indications. In other embodiments, the system 100 can include more or fewer display devices. For example, in addition to the display device 104 and the secondary display 226, the system 100 can include another display (e.g., a medical grade computer monitor) visible to the user wearing the display device 104.

Figure 3:
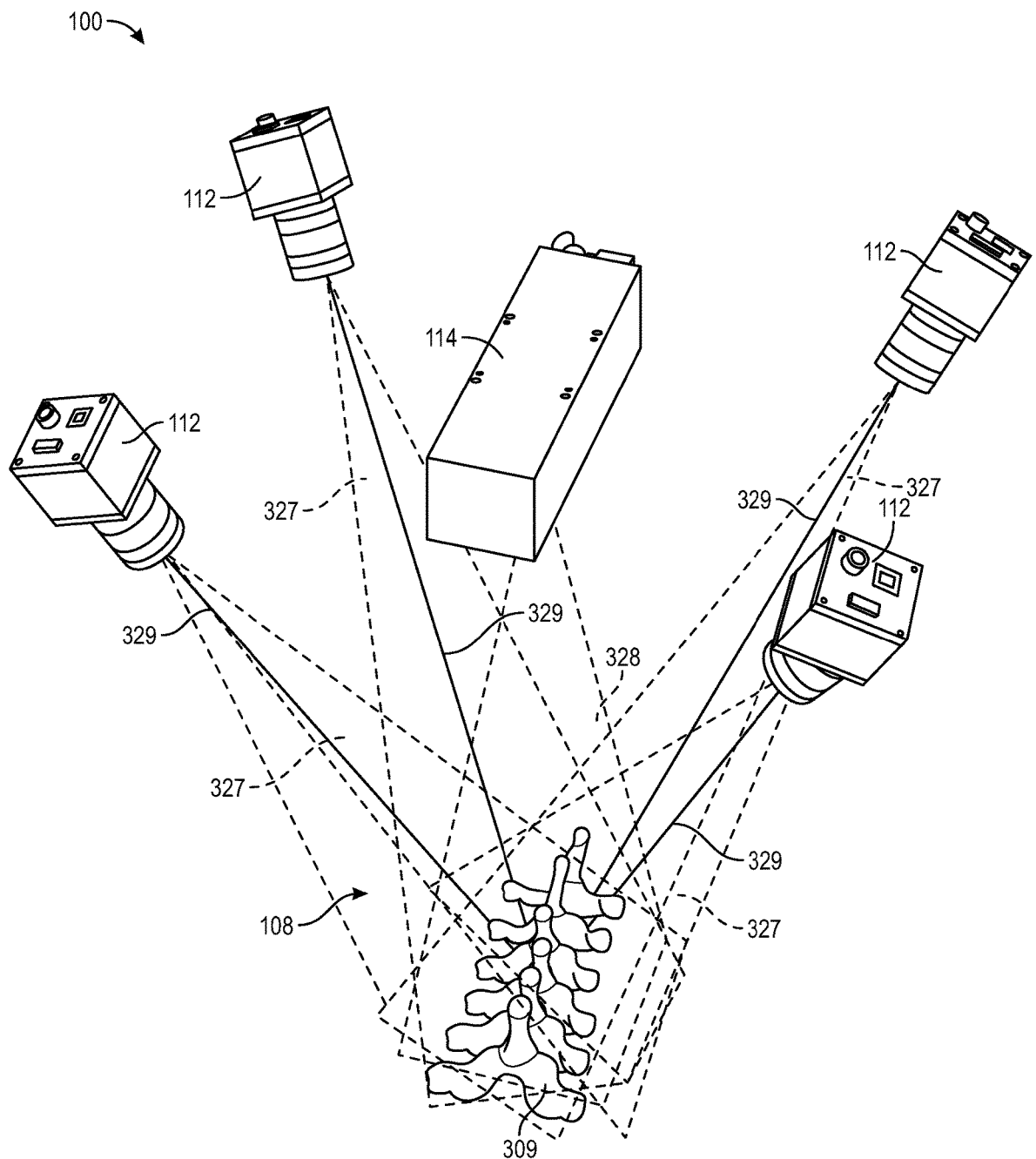
FIG. 3 is an isometric view of a portion of the imaging system of FIG. 1 illustrating four cameras of the imaging system in accordance with embodiments of the present technology.

FIG. 3 is an isometric view of a portion of the system 100 illustrating four of the cameras 112 in accordance with embodiments of the present technology. Other components of the system 100 (e.g., other portions of the camera array 110, the processing device 102, etc.) are not shown in FIG. 3 for the sake of clarity. In the illustrated embodiment, each of the cameras 112 has a field of view 327 and a focal axis 329. Likewise, the depth sensor 114 can have a field of view 328 aligned with a portion of the scene 108. The cameras 112 can be oriented such that the fields of view 327 are aligned with a portion of the scene 108 and at least partially overlap one another to together define an imaging volume. In some embodiments, some or all of the field of views 327, 328 at least partially overlap. For example, in the illustrated embodiment the fields of view 327, 328 converge toward a common measurement volume including a portion of a spine 309 of a patient (e.g., a human patient) located in/at the scene 108. In some embodiments, the cameras 112 are further oriented such that the focal axes 329 converge to a common point in the scene 108. In some aspects of the present technology, the convergence/alignment of the focal axes 329 can generally maximize disparity measurements between the cameras 112. In some embodiments, the cameras 112 and the depth sensor 114 are fixedly positioned relative to one another (e.g., rigidly mounted to a common frame) such that the positions of the cameras 112 and the depth sensor 114 relative to one another is known and/or can be readily determined via a calibration process. In other embodiments, the system 100 can include a different number of the cameras 112 and/or the cameras 112 can be positioned differently relative to another. In some embodiments, the camera array 110 can be moved (e.g., via the arm 222 of FIG. 2) to move the fields of view 327, 328 to, for example, scan the spine 309.

Referring to FIGS. 1-3 together, in some aspects of the present technology the system 100 can generate a digitized view of the scene 108 that provides a user (e.g., a surgeon) with increased "volumetric intelligence" of the scene 108. For example, the digitized scene 108 can be presented to the user from the perspective, orientation, and/or viewpoint of their eyes such that they effectively view the scene 108 as though they were not viewing the digitized image (e.g., as though they were not wearing the head-mounted display 104). However, the digitized scene 108 permits the user to digitally rotate, zoom, crop, or otherwise enhance their view to, for example, facilitate a surgical workflow. Likewise, initial image data, such as CT scans, can be registered to and overlaid over the image of the scene 108 to allow a surgeon to view these data sets together. Such a fused view can allow the surgeon to visualize aspects of a surgical site that may be obscured in the physical scene 108—such as regions of bone and/or tissue that have not been surgically exposed. Moreover, as described in further detail below with reference to FIGS. 4-11, the system 100 can determine one or more alignment parameters of the scene 108 (e.g., of the spine 309) in real-time or near real-time, and the alignment parameters can be presented to the user via the display device 104 for use in the surgical procedure. Such alignment parameters can further provide the user with "volumetric intelligence" about different volumes within the scene 108, including local, regional, spinal, and global parameters.

II. SELECTED EMBODIMENTS OF METHODS AND SYSTEMS FOR DETERMINING INTRAOPERATIVE ALIGNMENT PARAMETERS OF A SURGICAL TARGET, SUCH AS A SPINE

Figure 4A:
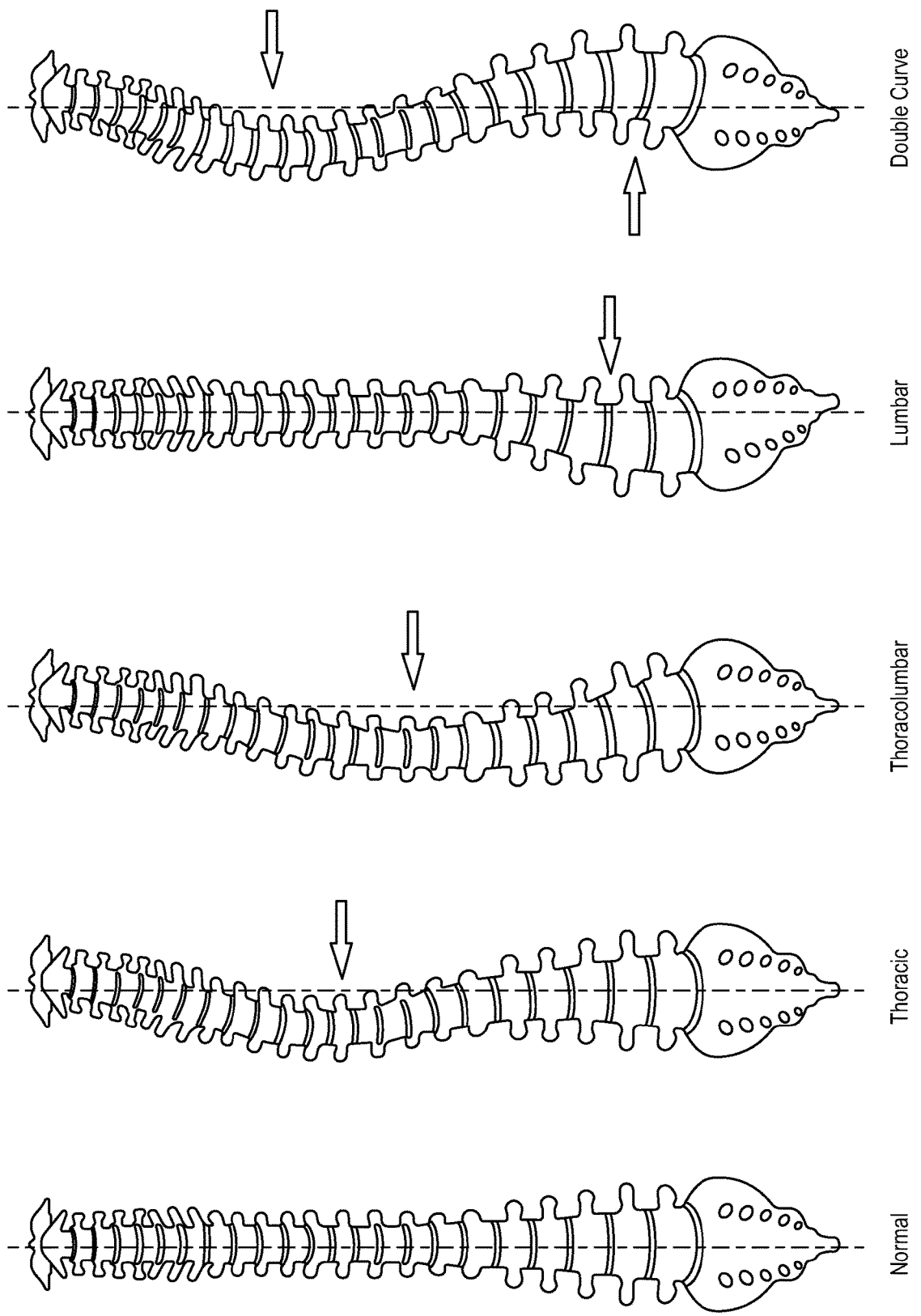
FIGS. 4A and 4B illustrate several different types of spinal deformities that may occur along the coronal plane and the sagittal plane, respectively, in accordance with embodiments of the present technology
Figure 4B:
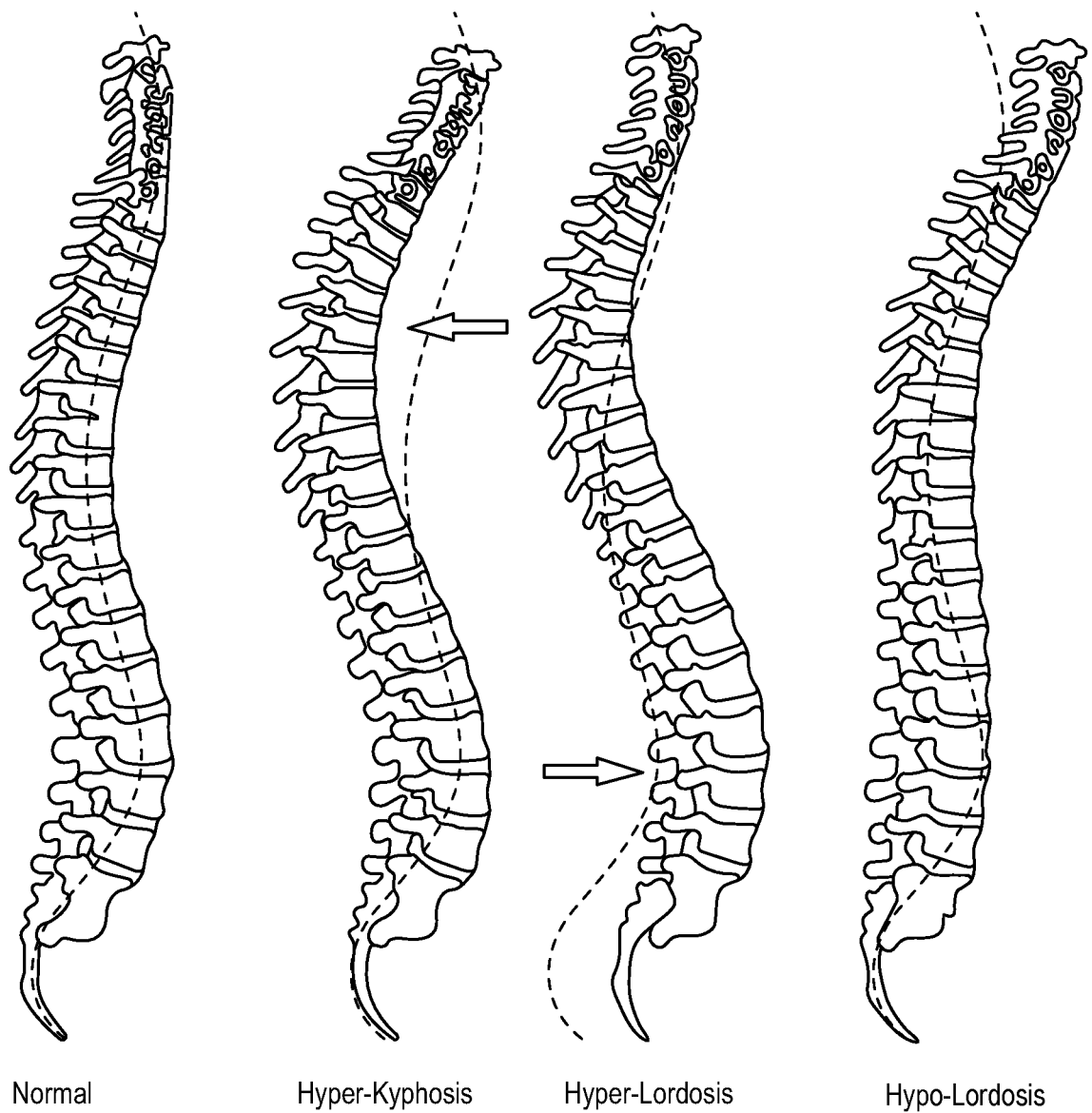

Spinal deformities involve pathologic curvatures of the spine and can occur naturally, or as a result of disease or damage to the spine. For example, FIGS. 4A and 4B illustrate several different types of spinal deformities that may occur along the coronal plane and the sagittal plane, respectively, in accordance with embodiments of the present technology. Spinal deformities can also exist in the axial plane. In some instances, spinal deformities can require surgical correction. Spinal surgery can be done by exposing a portion of the spine and/or via minimally invasive techniques.

Existing navigation systems for spine deformity surgery are limited to guiding the placement of hardware. Accordingly, surgeons must rely upon manual interpretation of either (i) the surgically exposed spine or (ii) intraoperative images (e.g., X-rays, CT images, fluoroscopic images) of the spine to assess the progress of the surgery, such as corrections to the spinal deformity. Subjective mental assessment of the exposed physical anatomy and the operative field by the surgeon is challenging and potentially imprecise/non-repeatable, introducing more of an "art" to the surgery. Although interpretation of existing 2D or 3D X-ray imaging may reduce the degree of subjectiveness in correction assessment, the image acquisition process interferes with the surgical workflow and exposes both the patient and surgical team to potentially harmful amounts of ionizing radiation. Also, the interpretation of 2D dimensional X-rays when the spinal alignment is a 3D issue can add to the art of creating spinal alignment.

Referring again to FIGS. 1-3 together, in some embodiments the system 100 can intraoperatively determine alignment parameters in substantially real-time without disturbing the surgical workflow and without the use of imaging modalities that rely on radiation. The system 100 can present the determined alignment parameters to the surgeon for use in evaluating the surgical procedure, and/or use the determined alignment parameters to automatically update a surgical plan or suggest updates to the surgical plan, thereby improving the accuracy and effectiveness of the surgical procedure.

Figure 5:
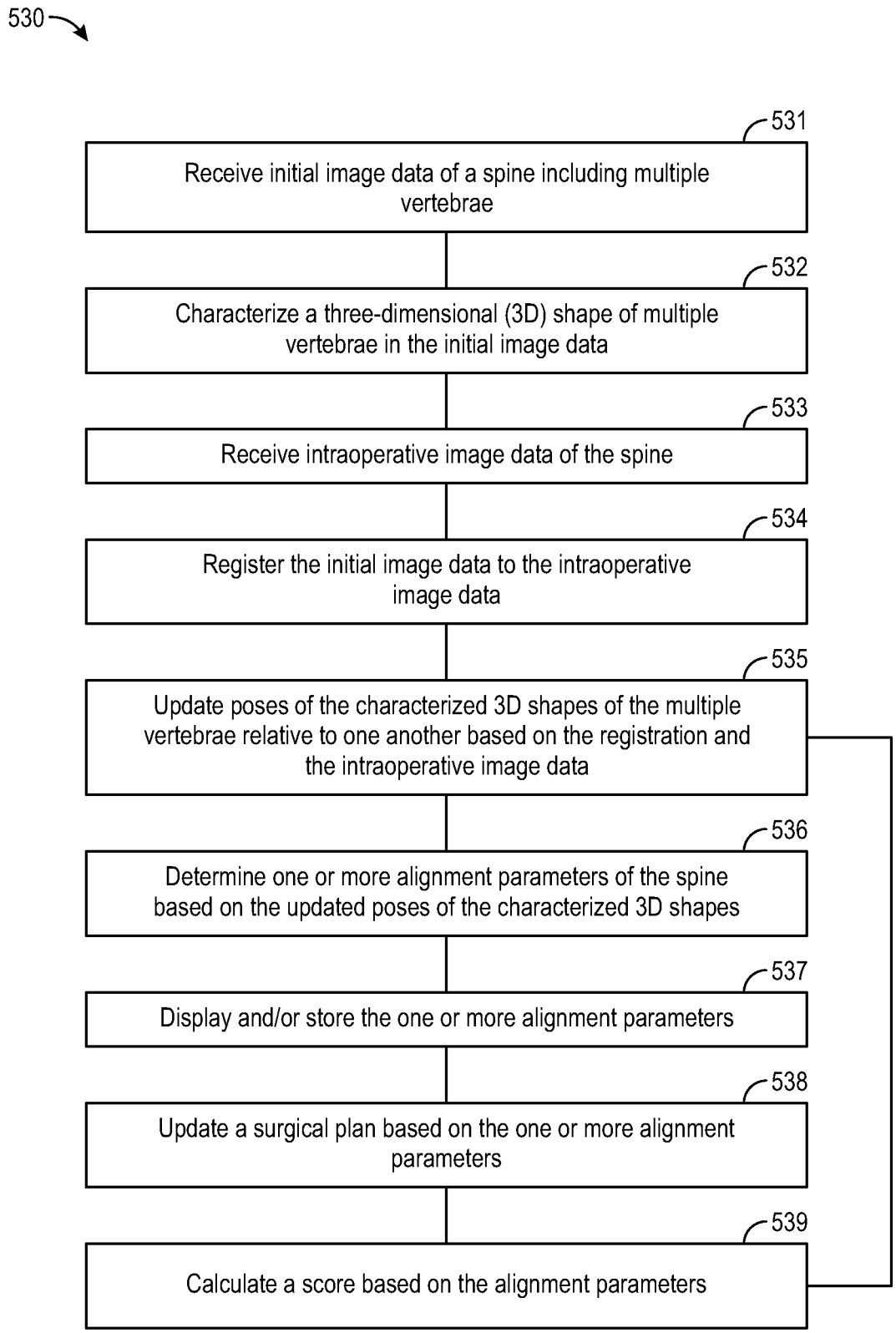
FIG. 5 is a flow diagram of a process or method for intraoperatively determining alignment parameters of a spine during a spinal surgical procedure in accordance with embodiments of the present technology.

More specifically, FIG. 5 is a flow diagram of a process or method 530 for intraoperatively determining alignment parameters of a spine during a spinal surgical procedure in accordance with embodiments of the present technology. Although some features of the method 530 are described in the context of the system 100 shown in FIGS. 1-3 for the sake of illustration, one skilled in the art will readily understand that the method 530 can be carried out using other suitable systems and/or devices described herein.

Moreover, although reference is primarily made to determining alignment parameters of a spine of a patient undergoing spinal surgery, in other embodiments the method 530 can be carried out to determine alignment parameters for other types of surgical targets (e.g., bone, flesh, ligaments) during other surgical procedures, such as orthopedic joint replacement surgery, cranial-based surgery, orthopedic trauma surgery, ear-nose-throat surgery, and so on, as described in further detail below. Similarly, while reference is made herein to initial image data, intraoperative image data, and a surgical scene, the method 530 can be used to determine alignment parameters for/within other types of scenes. For example, the method 530 can be used more generally to register any previously-captured image data to corresponding real-time or near-real-time image data of a scene to determine alignment parameters of a target within the scene.

At block 531, the method 530 can include receiving initial image data of a spine (e.g., the spine 309 of a human patient) including multiple vertebrae. In some embodiments, the initial image data is preoperative image data. As described in detail above, the preoperative image data can be, for example, medical scan data representing a 3D volume of a patient, such as computerized tomography (CT) scan data, magnetic resonance imaging (MRI) scan data, ultrasound images, fluoroscopic images, and/or the like. In some embodiments, the initial image data can be captured intraoperatively. For example, the initial image data can comprise 2D or 3D X-ray images, fluoroscopic images, CT images, MRI images, etc., and combinations thereof, captured of the patient within an operating room. In some embodiments, the initial image data comprises a point cloud, three-dimensional (3D) mesh, and/or another 3D data set. In some embodiments, the initial image data comprises segmented 3D CT scan data of some or all of the spine 309 (e.g., segmented on a per-vertebra basis).

Figure 6A:
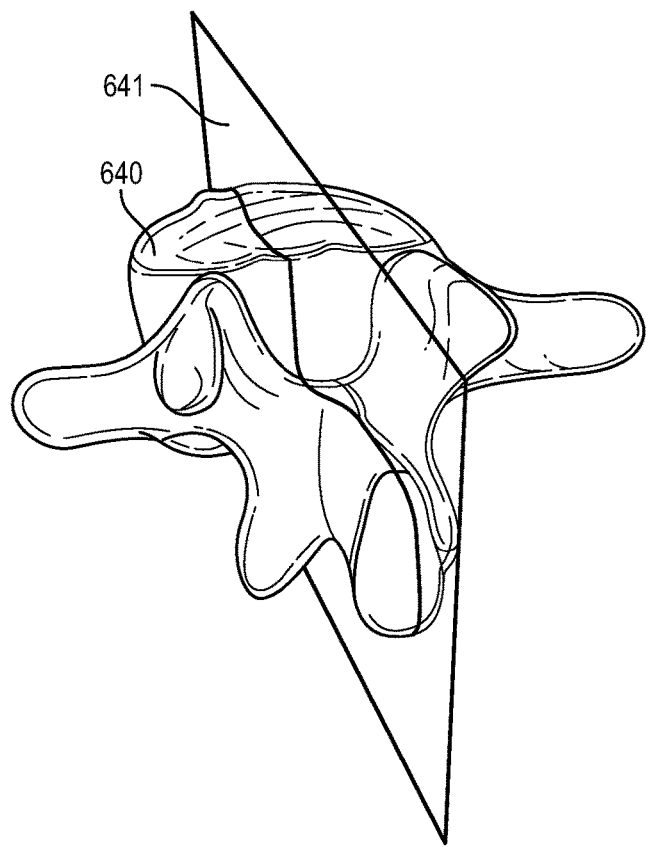
FIGS. 6A-6H are isometric views of a vertebra of a spine including various characterizations of a three-dimensional (3D) shape of the vertebra in accordance with embodiments of the present technology.
Figure 6B:
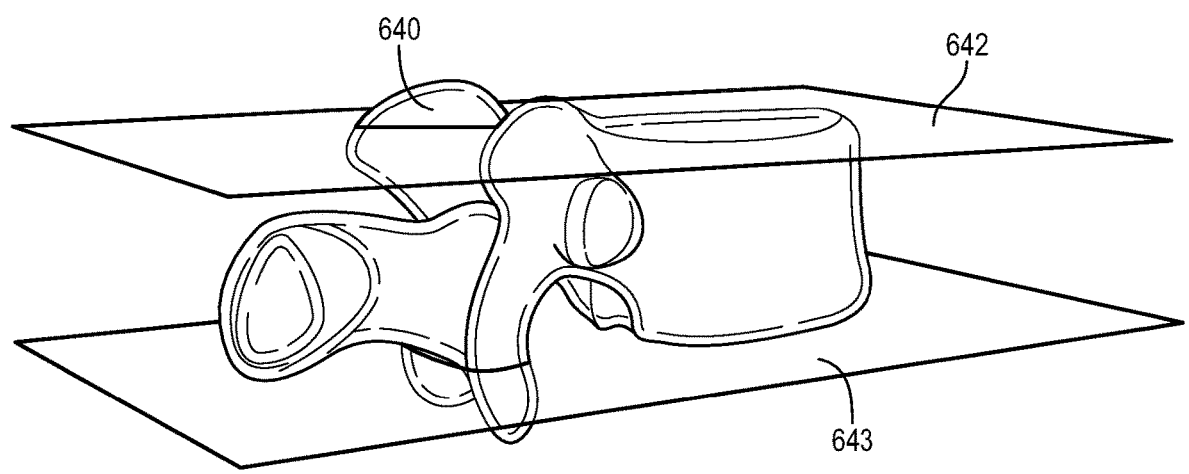
Figure 6C:
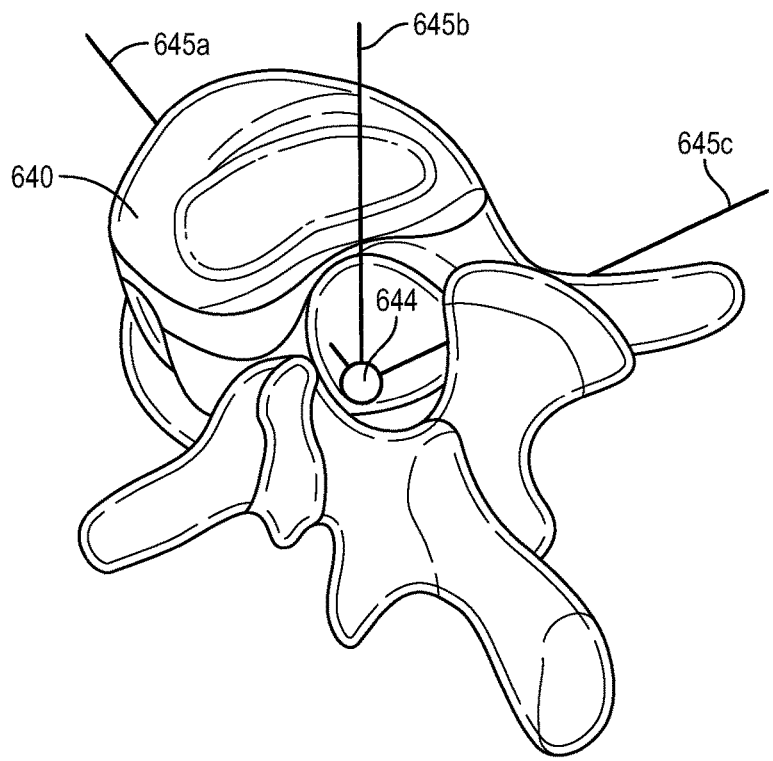
Figure 6D:
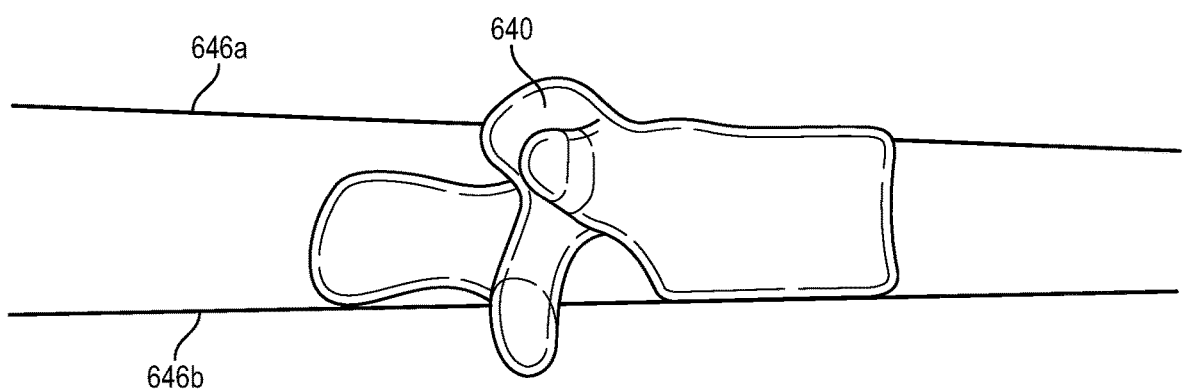
Figure 6E:
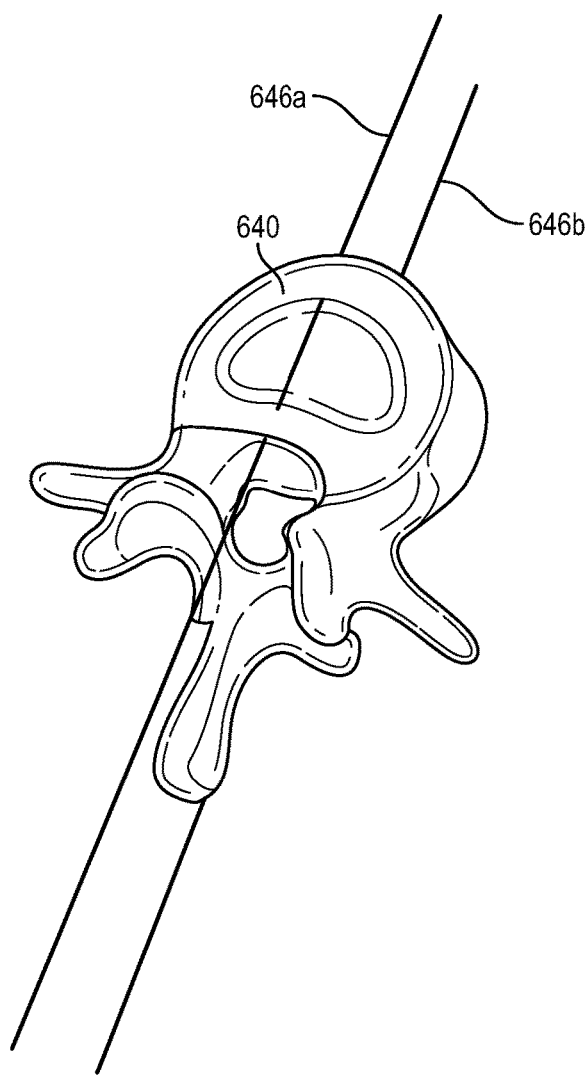
Figure 6F:
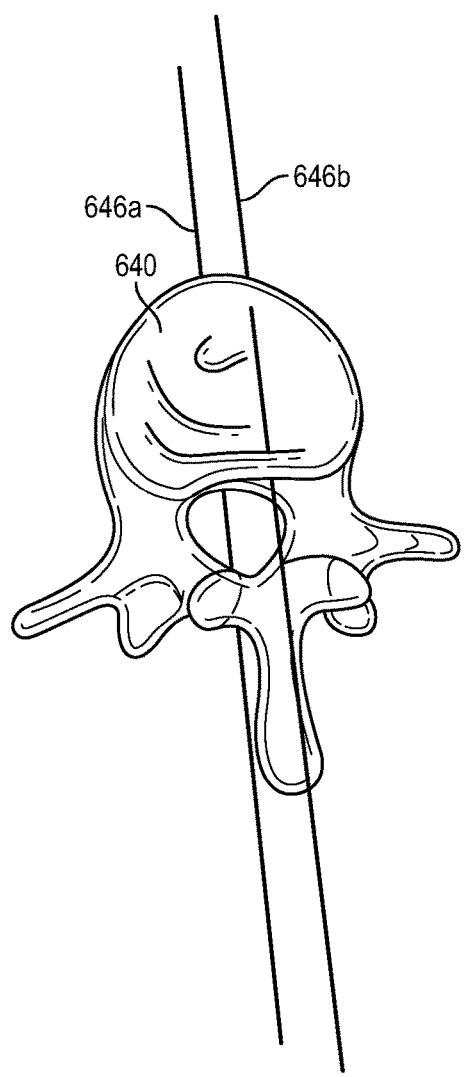
Figure 6G:
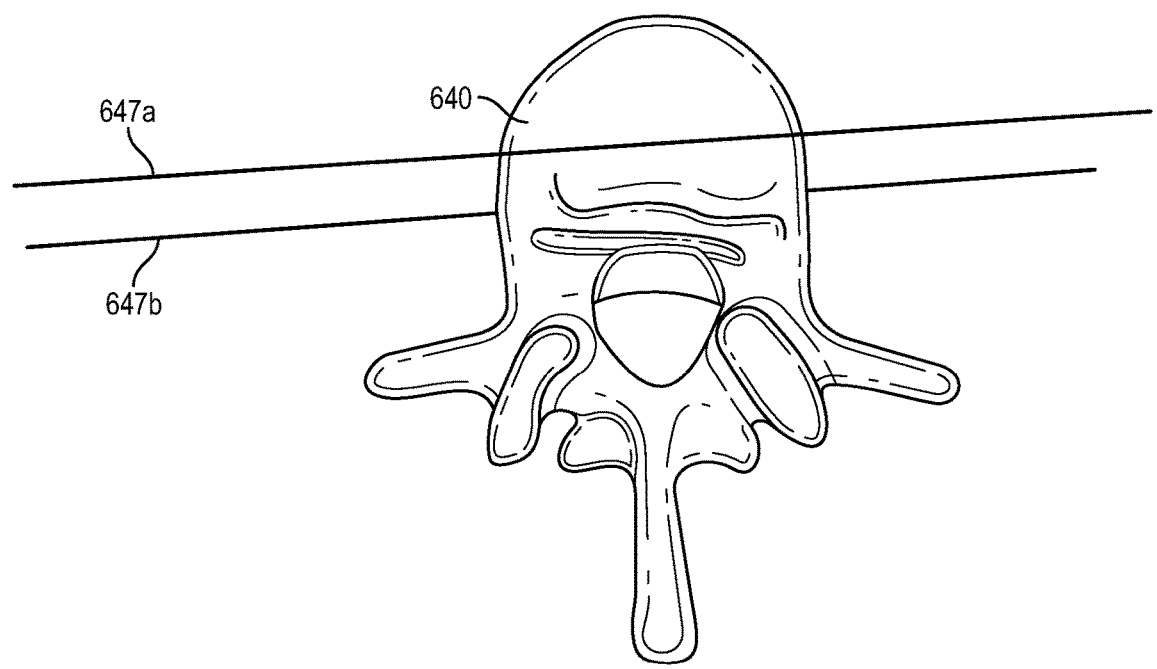
Figure 6H:
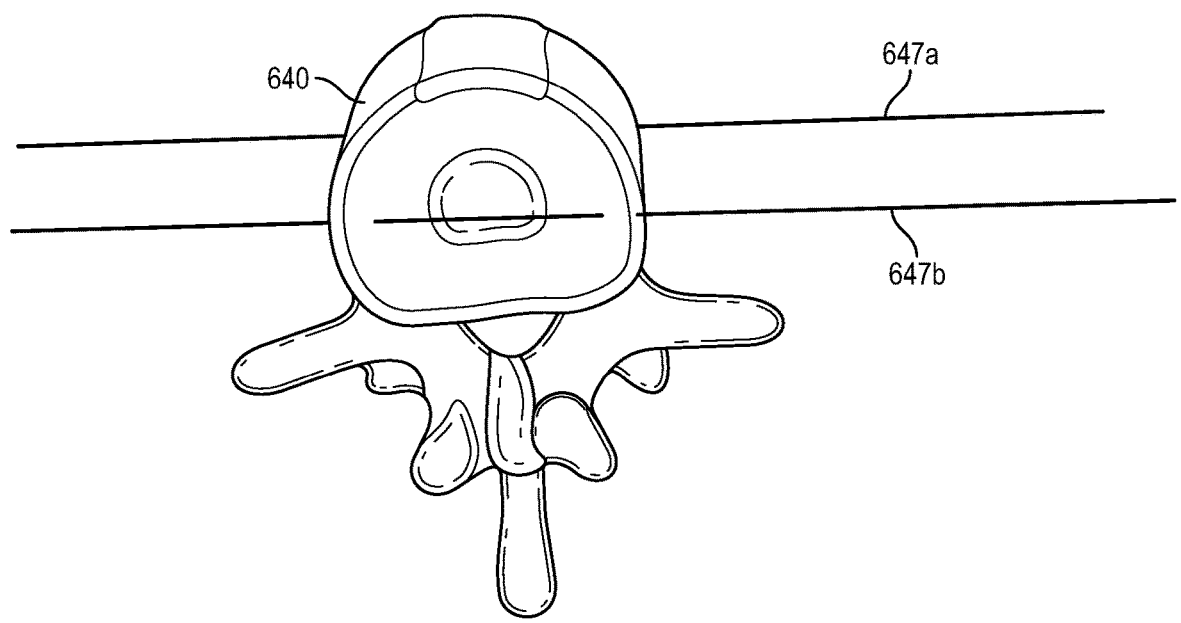

At block 532, the method 530 includes characterizing a 3D shape of multiple vertebrae of the spine 309 in the initial image data. In some embodiments, the characterizing includes identifying one or more geometric features of each vertebra or a subset of the vertebrae. For example, FIGS. 6A-6H are isometric views of a vertebra 640 of the spine 309 including various characterizations of the 3D shape of the vertebra in accordance with embodiments of the present technology. FIG. 6A illustrates a plane of symmetry 641 of the vertebra 640. FIG. 6B illustrates a superior endplate 642 and an inferior endplate 643 of the vertebra 640. FIG. 6C illustrates a local coordinate frame of the vertebra 640 including (i) an origin 644 generally centered with respect to the vertebra 640 and (ii) first through third orthogonal axes 644a-c, respectively, intersecting at the origin 644. FIGS. 6D-6F are a lateral view, a superior view, and inferior view, respectively, of the vertebra 640 illustrating first and second lines 646a-b, respectively. The lines 646a-b can be used to, for example, calculate sagittal curvature (e.g., lumbar lordosis) as described in greater detail below. FIGS. 6G and 6H are a superior view and an inferior view, respectively, of the vertebra 640 illustrating first and second lines 647a-b, respectively. The lines 647a-b can be used to, for example, calculate coronal curvature as described in greater detail below. The alignment processing device 109 can determine and store one or more of the geometric features of each vertebra including those shown in FIGS. 6A-6H and/or other geometric features, such as lines, planes, points, coordinates, and the like that may be useful in determining a degree of spinal curvature. The geometric features each have an initial pose (e.g., position and/or orientation) in the initial image data relative to one another.

At block 533, the method 530 can include receiving intraoperative image data of the surgical scene 108 including the spine 309 from the camera array 110. The intraoperative image data can include real-time or near-real-time images of the spine 309 in the scene 108 captured by the cameras 112 and/or the depth cameras 118. In some embodiments, the intraoperative image data includes (i) light field images from the cameras 112 and (ii) images from the depth cameras 118 that include encoded depth information about the scene 108. Some spinal deformities can be large enough that they are not entirely visible to the cameras 112 within the scene 108. Accordingly, in some embodiments receiving the intraoperative image data can include receiving intraoperative image data from the camera array 110 from different viewpoints relative to the scene 108 that capture the entire spinal deformity. For example, the camera array 110 can be moved (e.g., scanned) relative to the spine 309 to capture image data of the entire spine 309.

The initial image data and the intraoperative image data initially exist in different coordinate systems such that the same features in both data sets are represented differently. Accordingly, at block 534, the method 530 can include registering the initial image data to the intraoperative image data to, for example, establish a transform/mapping/transformation between the intraoperative image data and the initial image data such that these data sets can be represented in the same coordinate system. In some embodiments, the registration process matches (i) 3D points in a point cloud or a 3D mesh representing the initial image data to (ii) 3D points in a point cloud or a 3D mesh representing the intraoperative image data. In some embodiments, the system 100 (e.g., the registration processing device 105) generates a 3D point cloud or mesh from the intraoperative image data from the depth cameras 118 of the depth sensor 114, and registers the point cloud or mesh to the initial image data by detecting positions of fiducial markers and/or feature points visible in both data sets. For example, where the initial image data comprises CT scan data, rigid bodies of bone surface calculated from the CT scan data can be registered to the corresponding points/surfaces of the point cloud or mesh.

In some embodiments, the registration is based on/initiated by a surgeon or other user identifying corresponding points in both data sets. For example, the surgeon can identify points in the intraoperative image data that correspond to the same points in the initial image data, such as screw entry points identified by a preoperative plan. In some embodiments, the surgeon can identify the points by touching a tracked instrument to the spine 309. In other embodiments, the system 100 can employ other registration processes based on other methods of shape correspondence, and/or registration processes that do not rely on fiducial markers (e.g., markerless registration processes). In some embodiments, the registration/alignment process can include features that are generally similar or identical to the registration/alignment processes disclosed in (i) U.S. patent application Ser. No. 16/749,963, titled "ALIGNING PREOPERATIVE SCAN IMAGES TO REAL-TIME OPERATIVE IMAGES FOR A MEDIATED-REALITY VIEW OF A SURGICAL SITE," filed Jan. 22, 2020 and/or (ii) U.S. patent application Ser. No. 17/140,885, titled "METHODS AND SYSTEMS FOR REGISTERING PREOPERATIVE IMAGE DATA TO INTRAOPERATIVE IMAGE DATA OF A SCENE, SUCH AS A SURGICAL SCENE," and filed Jan. 4, 2021, each of which is incorporated herein by reference in its entirety. In some embodiments, the registration can be carried out using any feature or surface matching registration method, such as iterative closest point (ICP), Coherent Point Drift (CPD), or algorithms based on probability density estimation like Gaussian Mixture Models (GMM).

At block 535, the method 530 can include updating a pose (e.g., a position and/or orientation) of each of the characterized 3D shapes of the multiple vertebrae relative to one another based on the registration and the captured intraoperative image data. For example, the poses of any or all of the geometric features of the vertebrae (e.g., the planes of symmetry 641, the superior endplates 642, the inferior endplates 643, the local coordinate frames, the lines 646a-b, the lines 647a-b, etc.) can be updated relative to one another based on the registration and the currently captured intraoperative image data that reflects the current physical position and alignment of the spine 309. Accordingly, after updating, the geometric features are aligned relative to one another such that measurements between the geometric features reflect the physical geometry of the spine 309.

At block 536, the method 530 can include determining one or more alignment parameters of the spine 309 based on the updated poses of the characterized 3D shapes. In some embodiments, the alignment parameters are measurements between the identified geometric features (block 532) of one or more of the vertebrae. The alignment parameters can be local measurements of a single bone of the spine 309 (e.g., indicating an angulation between the superior and inferior endplates of a single vertebra), regional measurements of a portion of the spine 309 (e.g., indicating a curvature of a subset of the vertebrae of the spine), or can be spinal measurements (e.g., relating to the whole spine). The alignment parameters can include at least one of a Cobb angle (primary, secondary, and/or tertiary), lumbar lordosis measurement, thoracic kyphosis measurement, cervical lordosis measurement, sagittal vertical axis, pelvic tilt, pelvic angle, sacral slope, pelvic incidence, vertebral rotation angle, segmental lordosis/kyphosis measurement, anterior disc height, posterior disc height, foraminal height, foraminal area, disc volume, spondylolisthesis grading (e.g., in millimeter measurements and/or by Grade I, II, III, IV, and V), vertebral body height measurement (anterior, posterior, left, and/or right), C7 plumbline (C7PL), center sacral vertical line (CSVL), lateral olisthesis grading, sagittal vertical axis (SVA), T1 tilt, T1 pelvic angle, L1 tilt, L1 pelvic angle, etc.

In some embodiments, the alignment parameters can include 3D scoliotic parameters. Such 3D scoliotic parameters include vertebra centroid, vertebral body line, normal, apical vertebra/disc, end vertebra, vertebra axis system, trihedron axis system, spinal axis system, global axis system, vertebral plane, best fit plane, plane of maximum curvature, plane of minimum curvature, apical vertebra lateral plane, apical vertebra frontal plane, apical vertebra plane, vertebra lateral deviation, regional offset (balance), spinal length, curve lateral deviation, slenderness, spinal lateral deviation, frontal plane offset (frontal plane balance), sagittal plane offset (sagittal plane balance), maximum lateral deviation, vertebral transverse plane angulation (vertebral axial rotation), vertebral frontal plane angulation (vertebral lateral rotation), vertebral sagittal (median) plane angulation (vertebral flexion/extension), apical vertebra axial rotation, angle of best fit plane, angle of plane of maximum curvature, angle of plane of minimum curvature, apical angle, frontal plane offset angle, sagittal plane offset angle, frontal plane angular balance, geometric curvature, curvature angle, Cobb method, Ferguson method, analytic Cobb method, analytic Ferguson method, constrained curvature angle method, local geometric curvature, local curvature orientation, regional geometric curvature, curvature angle, local geometric torsion, local torsion orientation, local mechanical torsion, regional geometric torsion, regional mechanical torsion, etc.

Figure 7A:
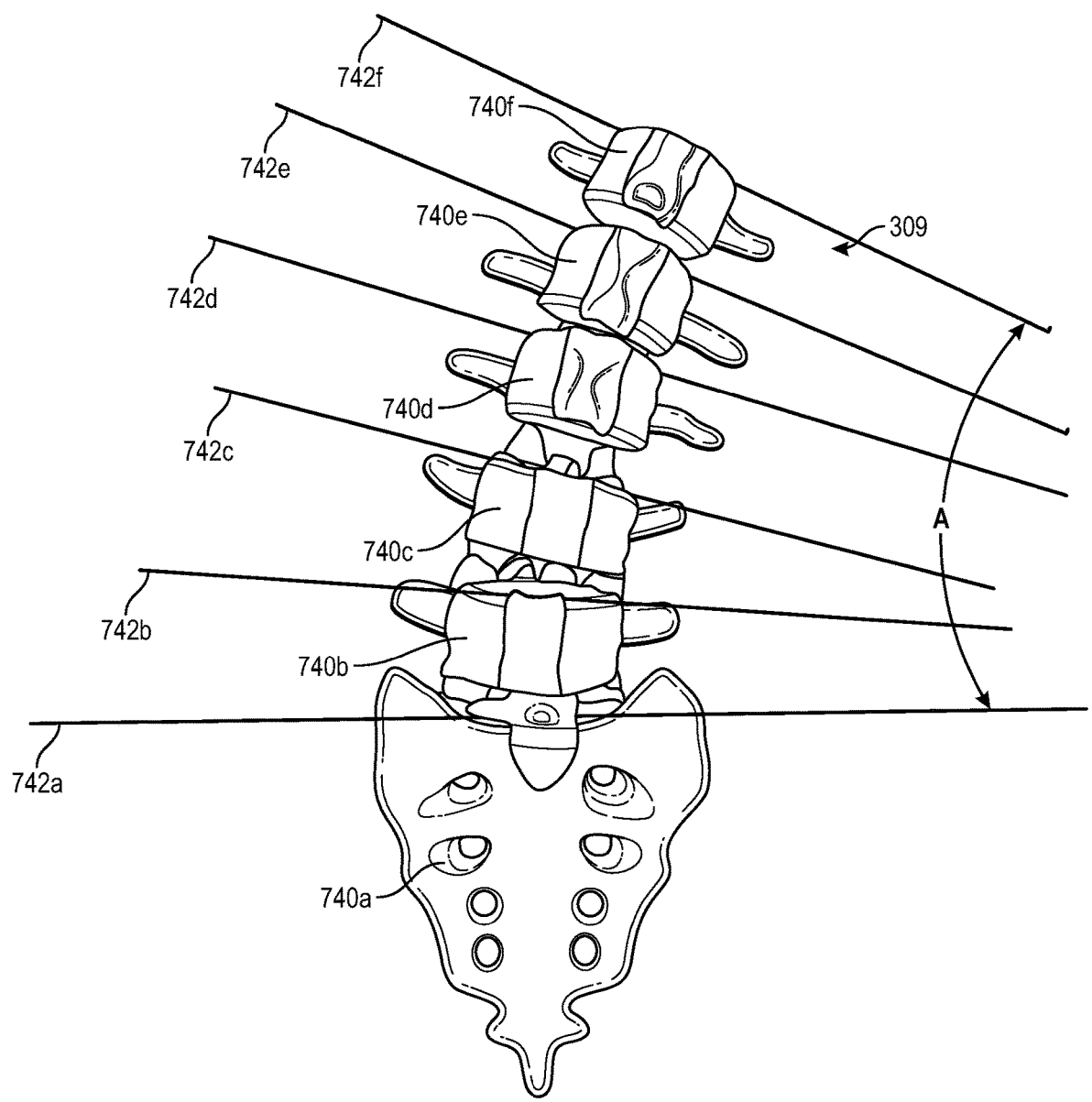
FIGS. 7A and 7B are an anterior view and a lateral view, respectively, of a spine including multiple vertebrae and corresponding superior endplates characterized in initial image data of the spine in accordance with embodiments of the present technology.
Figure 7B:
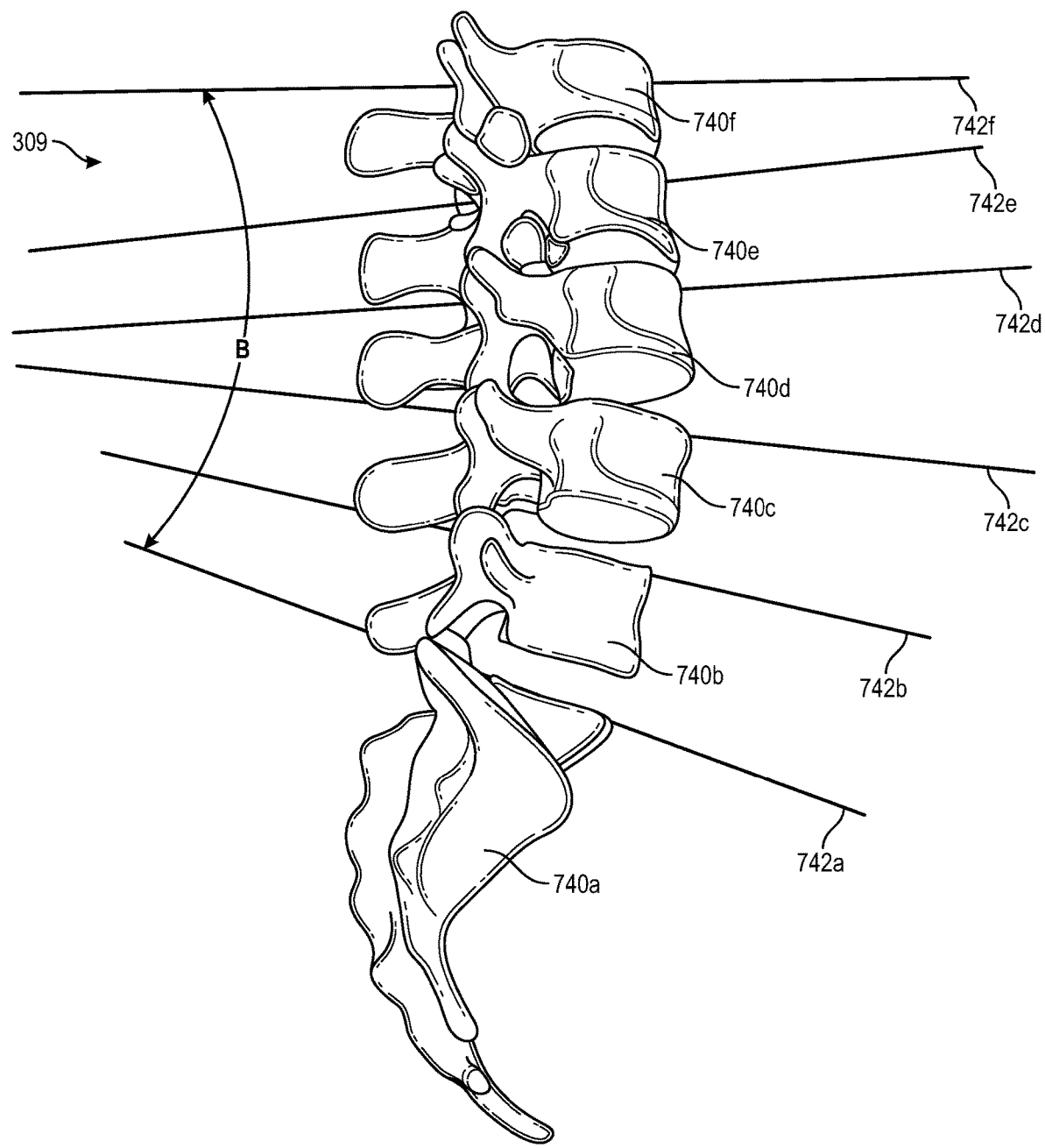

As one example, FIGS. 7A and 7B are an anterior view and a lateral view, respectively, of the spine 309 including multiple vertebrae 740 (identified individually as first through sixth vertebrae 740a-f, respectively) and corresponding superior endplates 742 (identified individually as first through sixth endplates 742a-f, respectively) characterized/identified in initial image data of the spine 309 in accordance with embodiments of the present technology. Referring to FIGS. 7A and 7B together, the first vertebra 740a can comprise a sacrum of the spine 309. The superior endplates 742 are geometric features of the vertebrae 740 (block 532) and have been updated in pose based on the registration (block 536). Referring to FIGS. 7A and 7B together, in some embodiments an angle (e.g., Cobb angle) can be calculated between any pair of the endplates 742. For example, an angle A shown in FIG. 7A between the first endplate 742a and the sixth end plate 742f along the coronal plane can provide a coronal Cobb angle measurement that is representative of spinal curvature in the coronal plane. Likewise, an angle B shown in FIG. 7B between the first endplate 742a and the sixth end plate 742f along the sagittal plane can provide a lumbar lordosis angle (which can also be referred to as a sagittal Cobb angle) measurement that is representative of spinal curvature in the sagittal plane. Other angles can be calculated between the endplates 742 of adjacent ones of the vertebrae 740 and/or between any pair (e.g., non-adjacent ones) of the endplates 742 depending on, for example, a region of interest of the spine 709. That is, the system 100 can calculate angles between any and all of the endplates 742, such as for adjacent vertebra (e.g., between the first vertebra 740a and the second vertebra 740b, between the second vertebra 740b and the third vertebra 740c, and so on) and/or for various pairs of non-adjacent vertebrae (e.g., between the first vertebra 740a and the fourth vertebra 740d, between the second vertebra 740b and the fifth vertebra 740e, and so on). In contrast, traditional alignment angle measurements are typically calculated using information from the starting and ending vertebrae of a curve using only initial image data and therefore do not reflect the current alignment of the spine during a surgical procedure.

Figure 8A:
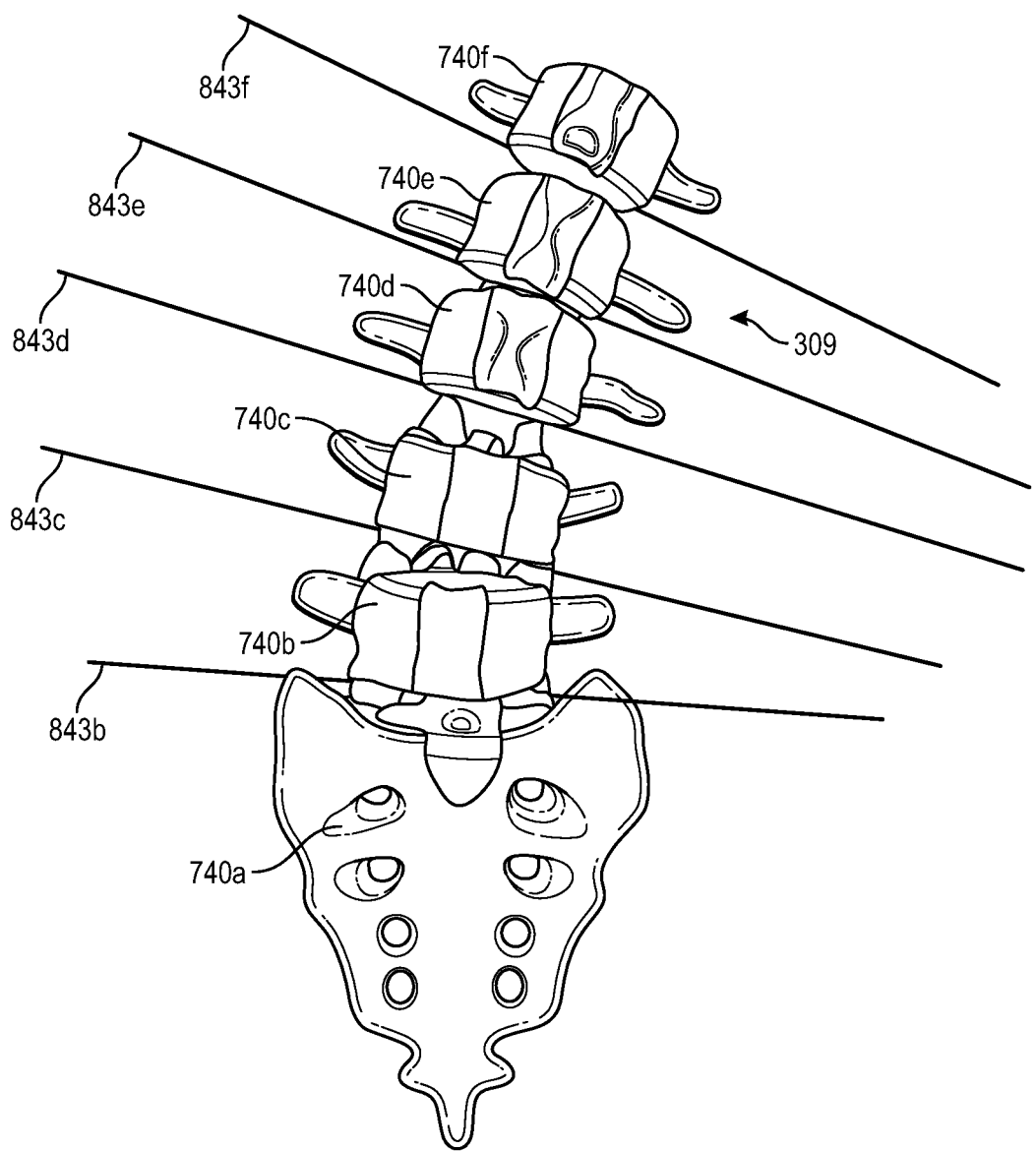
FIGS. 8A and 8B are an anterior view and a lateral view, respectively, of a spine including multiple vertebrae and corresponding inferior endplates characterized in initial image data of the spine in accordance with embodiments of the present technology.
Figure 8B:
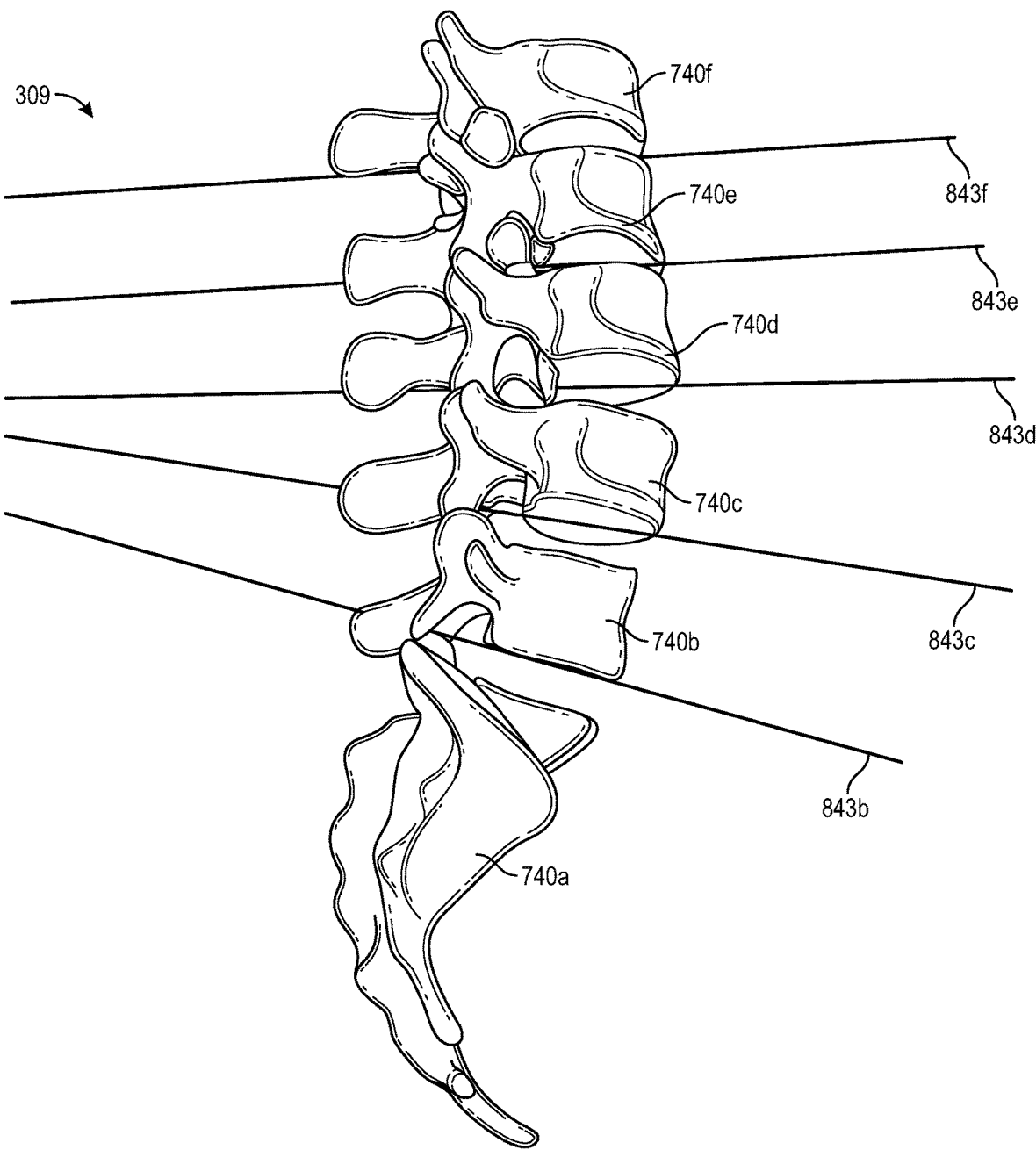

As another example, FIGS. 8A and 8B are an anterior view and a lateral view, respectively, of the spine 309 including inferior endplates 843 (identified individually as second through sixth endplates 843b-f, respectively) corresponding to the vertebrae 740 and characterized/identified in initial image data of the spine 309 in accordance with embodiments of the present technology. Referring to FIGS. 8A and 8B together, in some embodiments an inferior endplate is not generated for the sacrum 740a. In some embodiments, the system 100 can determine angles (e.g., Cobb angles) between the inferior endplates 843 as discussed in detail above with reference to FIGS. 7A and 7B.

In some embodiments, the system 100 can determine different alignment parameters by measuring between different identified geometric parameters associated with the vertebrae and/or by combining different calculated alignment parameters (e.g., to generate 3D scoliotic parameters). For example, referring to FIGS. 7A-8B together, the vertebrae 740 can be separated by discs (not shown), and the system 100 can calculate a distance, spacing, angle, and/or other measure between the superior endplates 742 and the inferior endplates 843 to estimate a size, spacing, volume, angle, and/or other measure of the discs. More specifically, for example, the system 100 can measure a distance and/or angle between the second superior endplate 742b and the third superior endplate 843c to estimate a size, volume, angle, and/or the like of the disc between the second vertebra 740b and the third vertebra 740c.

Although FIGS. 7A-8B illustrate the use of superior endplates 742 and inferior endplates 743 to measure angles between the vertebrae 740 and disc sizes, the system 100 can use any of the various geometric features shown in FIGS. 6A-6H and/or additional geometric features of the vertebrae 740 to measure any spinal alignment parameter listed above (or otherwise known in the art) and between any or all of the vertebrae 740. For example, the system 100 can automatically determine any one or more of the alignment parameters described in the "*Radiographic Measurement Manual*," 2008th edition, by the Spinal Deformity Study Group, edited by Michael F. O'Brien, and published by Medtronic Sofamor Danek on Jan. 1, 2005, which is incorporated by reference in its entirety herein.

Returning to FIG. 5, at block 537, the method 530 can include displaying and/or storing the alignment parameters. For example, the system 100 can display the alignment parameters in real-time or near real-time on the head-mounted display 104 and/or the secondary display 226 such that the alignment parameters are available to the surgeon and/or another user during the surgical procedure. In some aspects of the present technology, this can allow the surgeon to know in real-time or near real-time what effect their surgical action (e.g., implantation of a pedicle screw or other implant) had on the alignment of the spine 309. In contrast, conventional navigation systems cannot provide such feedback during the surgical procedure to present to the surgeon the effect of their actions. Similarly, the system 100 can store the alignment parameters as a function over time such that the effect of the surgical procedure can be analyzed after the surgical procedure.

At block 538, the method 530 can optionally include updating a surgical plan based on the determined alignment parameters. The system 100 can automatically generate and implement the updates to the surgical plan and/or suggest the updates to the user. For example, if the surgeon was expecting a certain correction in alignment after operating on a particular vertebra of the spine 309, but the alignment parameters indicate that such a correction was not achieved, the system 100 can update the surgical plan to account for the discrepancy between the expected and actual corrections. For example, the system 100 can use the determined alignment features and the associated relative pose information of the vertebrae to propose specific adjustments to each vertebra so that they are optimal to some specific measurement (e.g., minimal average Cobb angle between adjacent vertebrae). In some embodiments, this is done by optimizing over possible updates to the alignment of the spine 309 with an appropriate cost function (e.g., in an analogous manner to inverse kinematics in robotic control). For example, in some embodiments the system 100 can use intraoperatively determined alignment parameters related to disc spacing to aid surgeons in selecting an interbody device size and/or choosing an appropriate amount of interbody injection material (e.g., bone graft).

At block 539, the method 530 can optionally include calculating a score, formula, or the like based on the alignment parameters. For example, the score can be a global alignment and proportion (GAP) score, which analyzes the sagittal plane based on pelvic-incidence-based proportional parameters and predicts mechanical complications in patients undergoing surgery for adult spinal deformity. Further details for calculating such a GAP score are described in the "*Global Alignment and Proportion (GAP) Score: Development and Validation of a New Method of Analyzing Spinopelvic Alignment to Predict Mechanical Complications After Adult Spinal Deformity Surgery,*" by C. Yilgor et al., published in volume 99 issue 19 of the Journal of Bone and Joint Surgery on Oct. 4, 2017 and on pages 1661-1672, which is incorporated by reference in its entirety herein.

Further, in some embodiments the method 530 can return to block 535 after any of blocks 536-539 to again update the poses of the characterized 3D shapes of the multiple vertebrae. In this manner, the system 100 can continuously update the alignment parameters in real-time or near real-time to reflect the current alignment of the spine 309 and track the progression of the alignment of the spine 309 during the spinal surgical procedure. For example, FIGS. 9A-9E illustrate a progression of outputs/data captures of the system 100 during a spinal surgical procedure on a spine to correct a spinal deformity including updated alignment parameters in accordance with embodiments of the present technology.

Figure 9A:
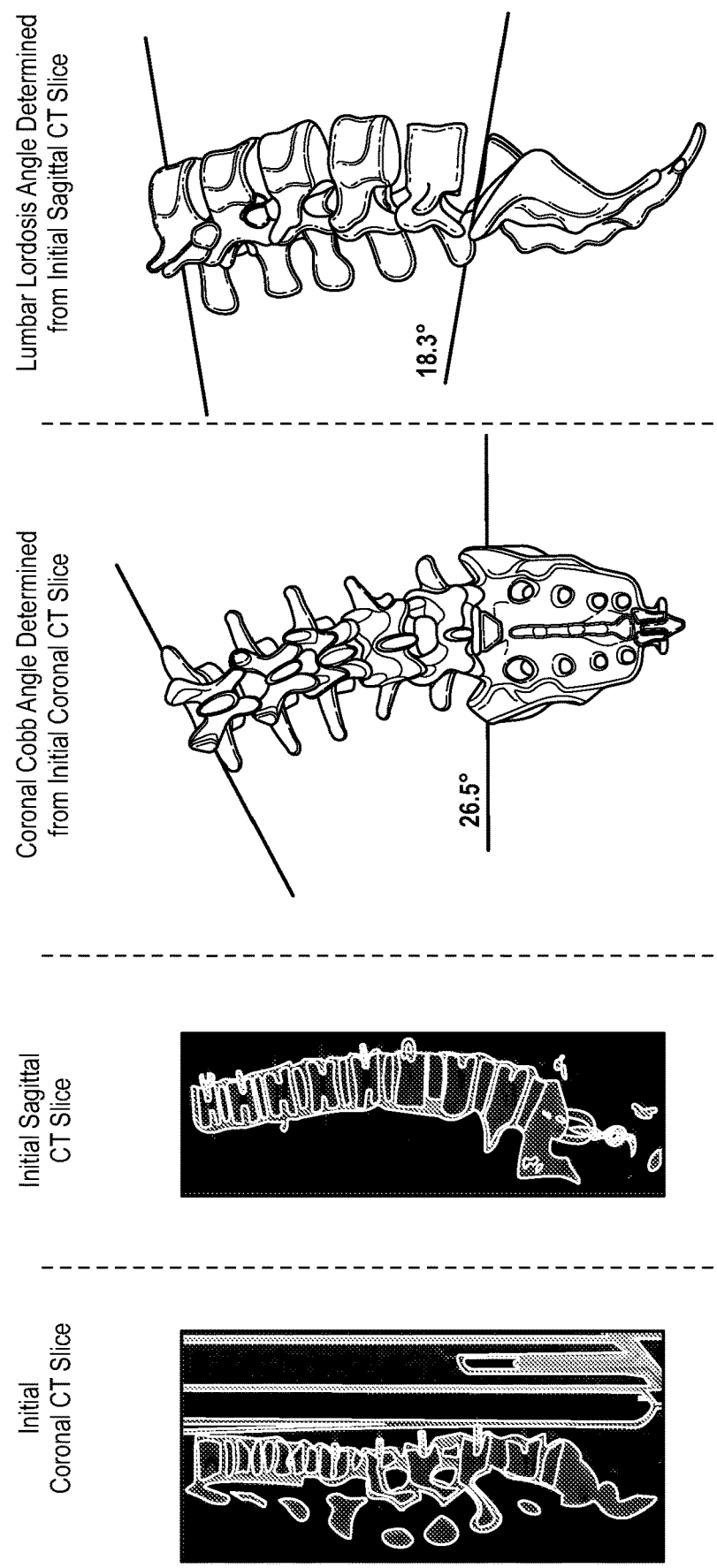
FIGS. 9A-9E illustrate a progression of outputs/data captures of the system of FIG. 1 during a spinal surgical procedure on a spine to correct a spinal deformity including updated alignment parameters in accordance with embodiments of the present technology.

FIG. 9A illustrates an initial coronal CT slice of the spine, an initial sagittal CT slice of the spine, a coronal Cobb angle determined from the initial coronal CT slice, and a lumbar lordosis angle determined from the initial sagittal CT slice. The initial coronal and sagittal CT slices can be captured preoperatively or intraoperatively, such as at the beginning of the spinal surgical procedure (e.g., after surgically exposing the spine). The coronal Cobb angle and the lumbar lordosis angle can be determined manually by a user using conventional methods, or can be determined automatically by the system 100 by calculating alignment parameters (block 536) of the spine based on the initial poses of the vertebrae of the spine in the initial image data. In the illustrated embodiment, the spine has a deformity including a curvature having a coronal Cobb angle of 26.5° and a lumbar lordosis angle of 18.3°.

Figure 9B:
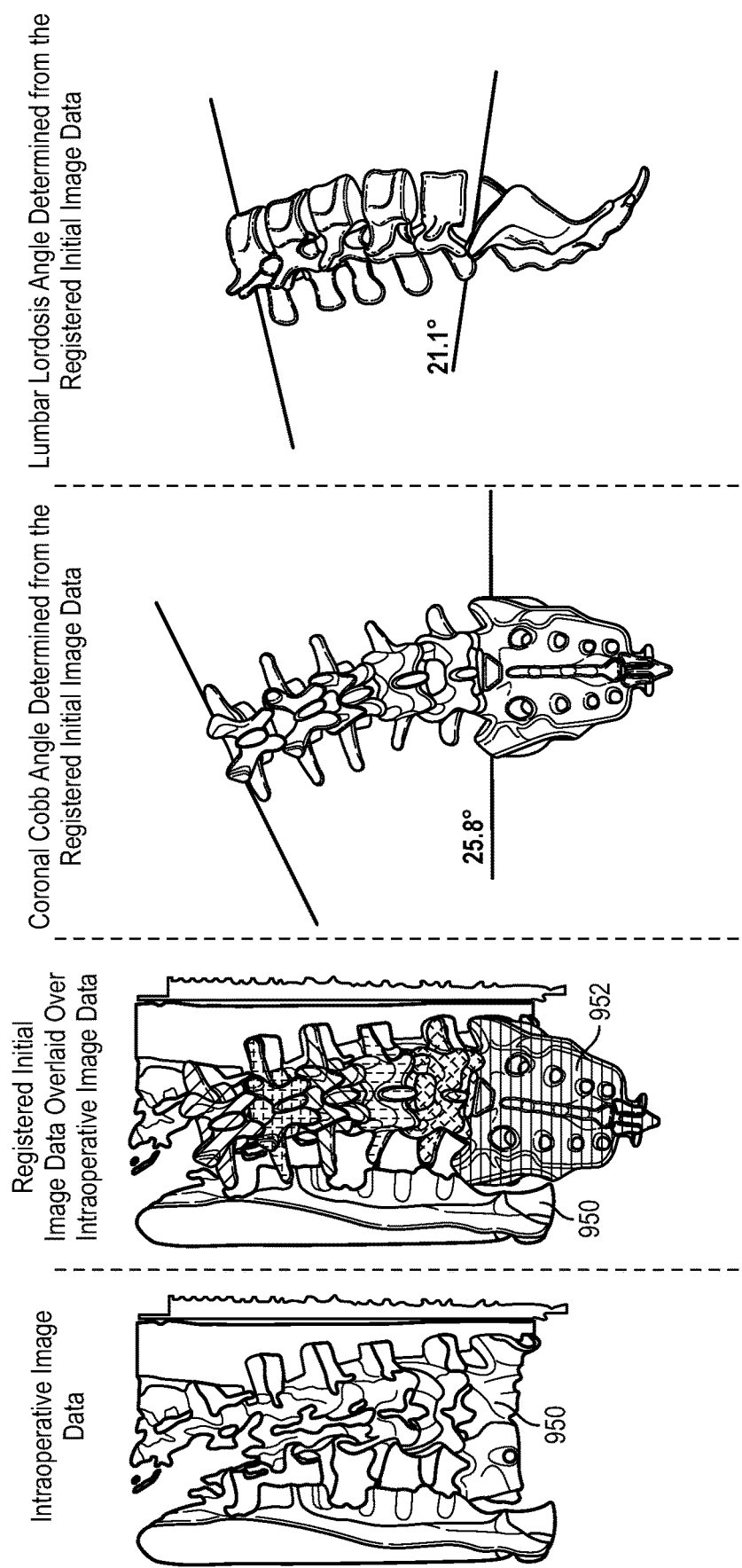

FIG. 9B illustrates intraoperatively captured image data 950 of the spine, initial image data 952 of the spine overlaid over the intraoperative image data 950 after registration, a coronal Cobb angle determined from the registered initial image data 952, and a lumbar lordosis angle determined from the registered initial image data 952 at a first time during the surgical procedure on the spine. The first time can be after the surgeon operates on a first vertebra of the spine to correct the deformity. The system 100 can update the poses of the vertebrae of the spine (block 535) relative to one another based on the registration (e.g., based on the physical positioning of the spine captured in the intraoperative image data 950). As described in detail above, the intraoperative image data 950 can include real-time or near-real-time images of the spine 309 in the scene 108 captured by the cameras 112 and/or the depth cameras 118 of the camera array 110. In some embodiments, the intraoperative image data includes (i) light field images from the cameras 112 and (ii) images from the depth cameras 118 that include encoded depth information about the scene 108.

Figure 9C:
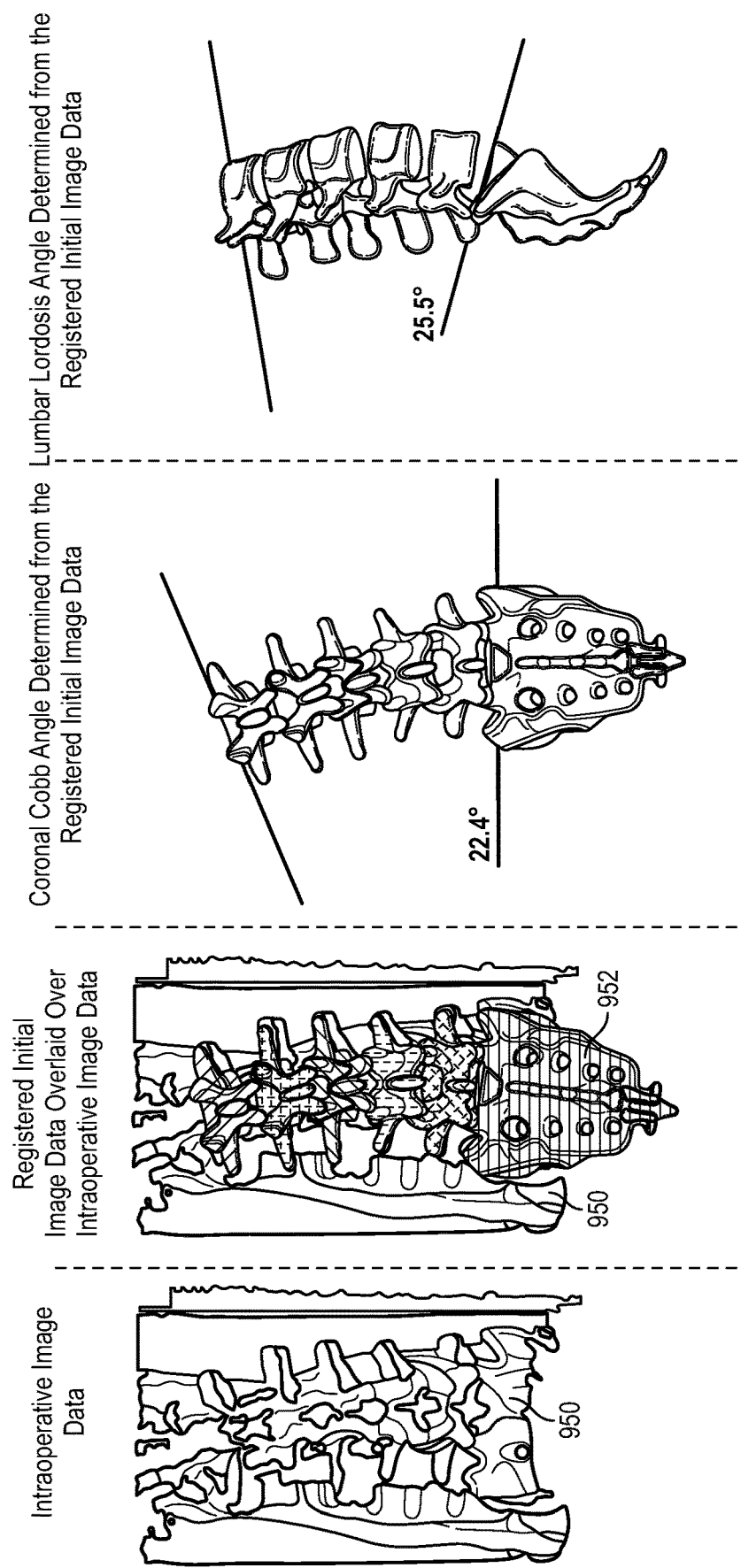

After registration, the initial image data 952 and the intraoperative image data 950 are aligned in the same coordinate system and can be overlaid over one another. Based on the updated poses of the characterized 3D shapes of the vertebrae of the spine (block 535), the system 100 can determine (block 536) the updated coronal Cobb angle (e.g., 25.8°) and the updated lumbar lordosis angle (e.g., 21.1°) at the first time during the surgical procedure along with any one or more different alignment parameters of the spine. For example, the system 100 can calculate the angle between one or more endplates identified in the initial image data (e.g., as described in detail above with reference to FIGS. 7A-8B) that characterize the 3D shapes of the vertebrae. In the illustrated embodiment, the determined coronal Cobb and lumbar lordosis angles indicate that the surgical procedure has decreased the coronal Cobb angle and increased the lumbar lordosis angle relative to the initial alignment of the spine (FIG. 9A). Similarly, the determined coronal Cobb and lumbar lordosis angles can indicate that the surgical procedure has changed (e.g., improved) the angles toward a surgical goal or plan. In some embodiments, the determined coronal Cobb and lumbar lordosis angles are displayed to the surgeon to provide real-time or near real-time feedback (e.g., provided at the first time) on the effectiveness of the surgical procedure in correcting the deformity FIG. 9C illustrates the intraoperatively captured image data 950 of the spine, the initial image data 952 of the spine overlaid over the intraoperative image data 950 after registration (block 534) and updating of the poses of the characterized shapes of the vertebrae (block 535), the coronal Cobb angle determined from the registered initial image data 952, and the lumbar lordosis angle determined from the registered initial image data 952 at a second time during the surgical procedure on the spine. The second time can be later than the first time, such as after the surgeon operates on a second vertebra of the spine after the first vertebra to correct the deformity. Based on the updated poses of the characterized 3D shapes of the vertebrae of the spine (block 535), the system 100 can determine (block 536) the updated coronal Cobb angle (e.g., 22.4°) and the updated lumbar lordosis angle (e.g., 25.5°) at the second time during the surgical procedure along with any one or more different alignment parameters of the spine. In the illustrated embodiment, the determined coronal Cobb and lumbar lordosis angles indicate that the surgical procedure has decreased the coronal Cobb angle and increased the lumbar lordosis angle relative to the alignment of the spine at the first time during the surgical procedure (FIG. 9B). Similarly, the determined coronal Cobb and lumbar lordosis angles can indicate that the surgical procedure has changed (e.g., improved) the angles toward a surgical goal or plan. In some embodiments, the determined coronal Cobb and lumbar lordosis angles are displayed to the surgeon to provide real-time or near real-time (e.g., provided at the second time) feedback on the effectiveness of the surgical procedure in correcting the deformity.

Figure 9D:
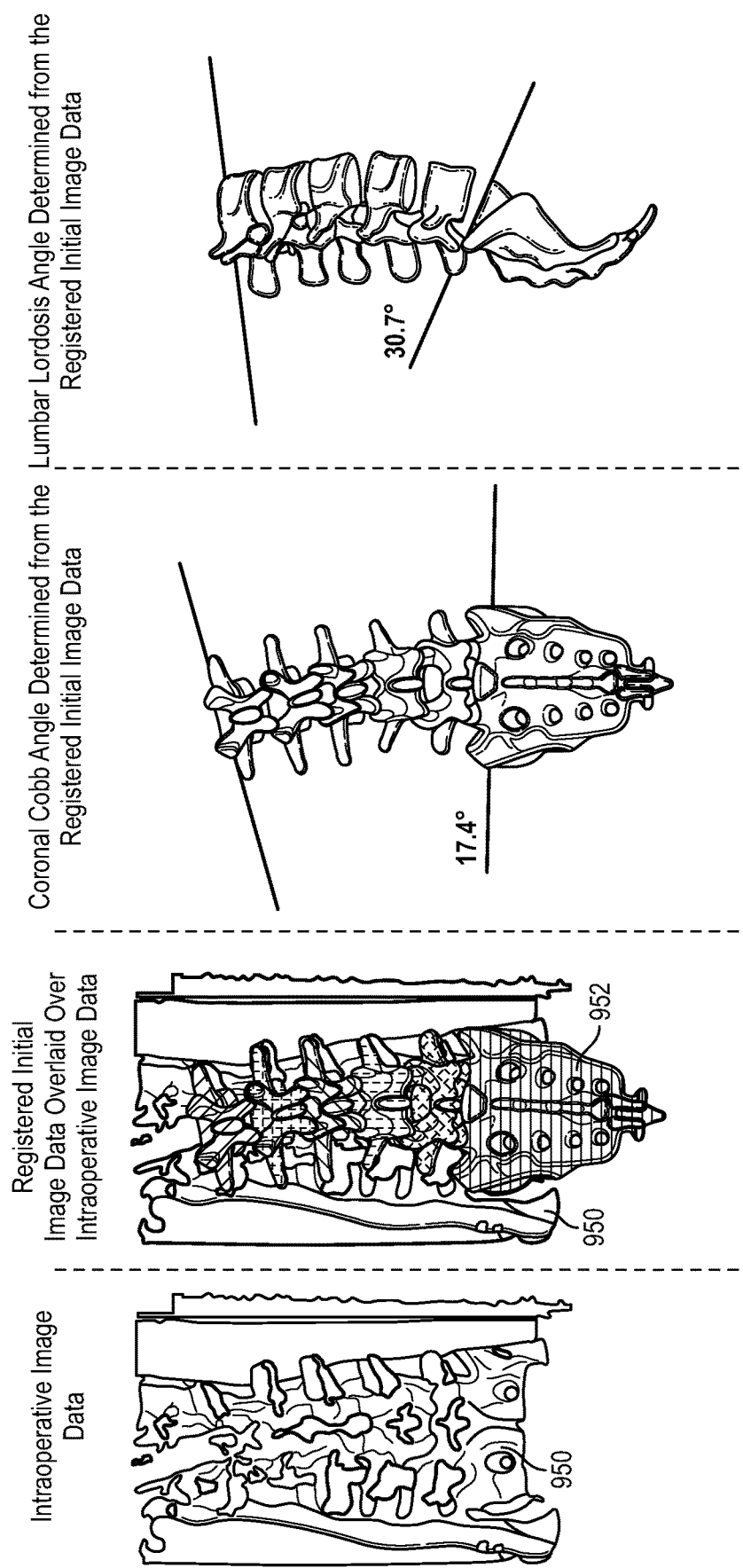
Figure 9E:
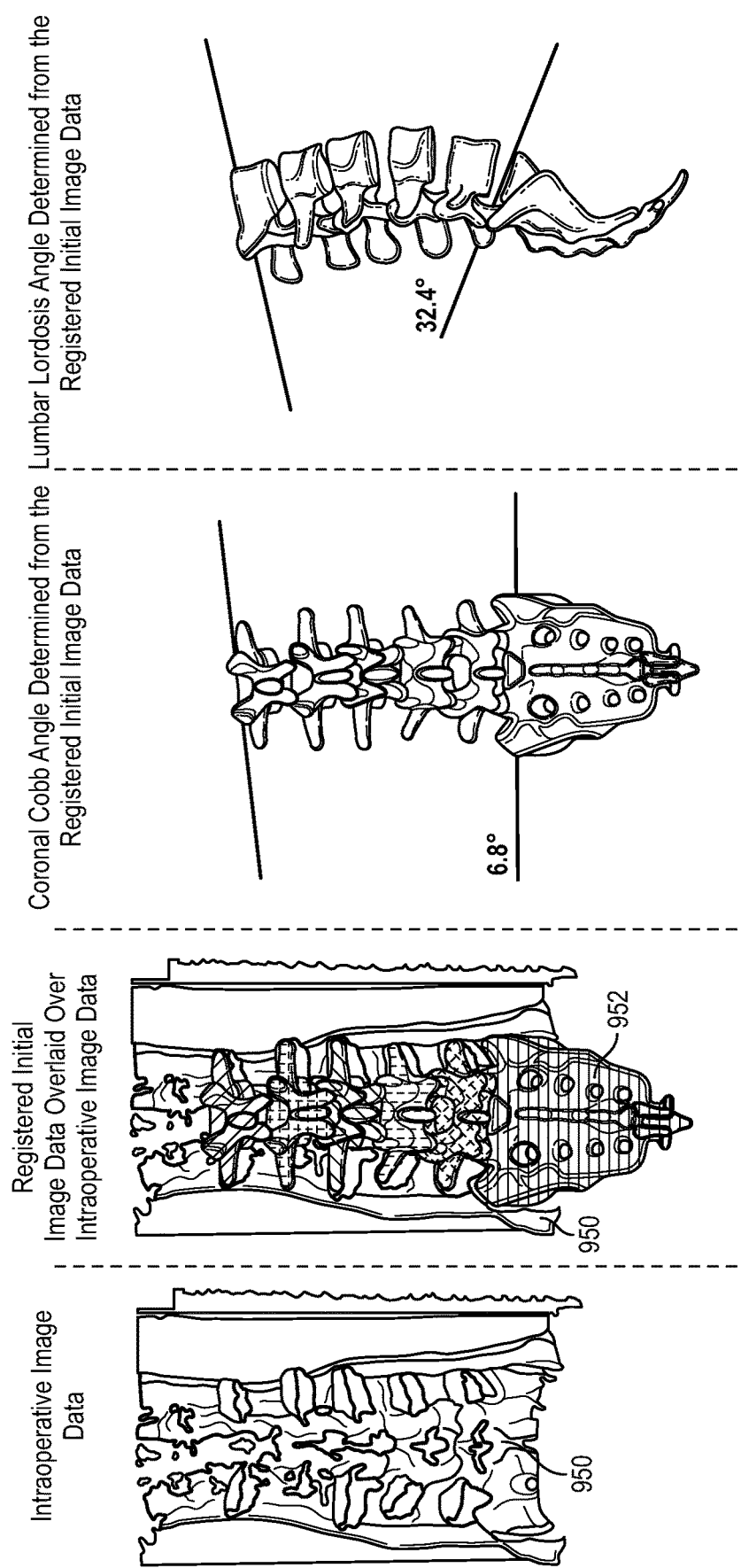

Similarly, FIG. 9D illustrates the intraoperatively captured image data 950 of the spine, the initial image data 952 of the spine overlaid over the intraoperative image data 950 after registration (block 534) and updating of the poses of the characterized shapes of the vertebrae (block 535), the coronal Cobb angle determined from the registered initial image data 952, and the lumbar lordosis angle determined from the registered initial image data 952 at a third time during the surgical procedure on the spine. The third time can be later than the second time, such as after the surgeon operates on a third vertebra of the spine after the first and second vertebrae to correct the deformity and/or places one or more interbody devices. Based on the updated poses of the characterized 3D shapes of the vertebrae of the spine (block 535), the system 100 can determine (block 536) the updated coronal Cobb angle (e.g., 17.4°) and the updated lumbar lordosis angle (e.g., 30.7°) at the third time during the surgical procedure along with any one or more different alignment parameters of the spine. In the illustrated embodiment, the determined coronal Cobb and lumbar lordosis angles indicate that the surgical procedure has decreased the coronal Cobb angle and increased the lumbar lordosis angle relative to the alignment of the spine at the second time during the surgical procedure (FIG. 9C). Similarly, the determined coronal Cobb and lumbar lordosis angles can indicate that the surgical procedure has changed (e.g., improved) the angles toward the surgical goal or plan. In some embodiments, the determined coronal Cobb and lumbar lordosis angles are displayed to the surgeon to provide real-time or near real-time (e.g., provided at the third time) feedback on the effectiveness of the surgical procedure in correcting the deformity Lastly, FIG. 9E illustrates the intraoperatively captured image data 950 of the spine, the initial image data 952 of the spine overlaid over the intraoperative image data 950 after registration (block 534) and updating of the poses of the characterized shapes of the vertebrae (block 535), the coronal Cobb angle determined from the registered initial image data 952, and the lumbar lordosis angle determined from the registered initial image data 952 at a fourth time during the surgical procedure on the spine. The fourth time can be later than the third time, such as after the surgeon operates on a fourth vertebra of the spine after the first, second, and third vertebrae to correct the deformity. Based on the updated poses of the characterized 3D shapes of the vertebrae of the spine (block 535), the system 100 can determine (block 536) the updated coronal Cobb angle (e.g., 6.8°) and the updated lumbar lordosis angle (e.g., 32.4°) at the fourth time during the surgical procedure along with any one or more different alignment parameters of the spine. In the illustrated embodiment, the determined coronal Cobb and lumbar lordosis angles indicate that the surgical procedure has decreased the coronal Cobb angle and increased the lumbar lordosis angle relative to the alignment of the spine at the third time during the surgical procedure (FIG. 9D). Similarly, the determined coronal Cobb and lumbar lordosis angles can indicate that the surgical procedure has changed (e.g., improved) the angles toward the surgical goal or plan. In some embodiments, the determined coronal Cobb and lumbar lordosis angles are displayed to the surgeon to provide real-time or near real-time (e.g., provided at the fourth time) feedback on the effectiveness of the surgical procedure in correcting the deformity. In some embodiments, the determined coronal Cobb and lumbar lordosis angles at the fourth time illustrated in FIG. 9E can indicate to the surgeon that the curvature has been sufficiently straightened (e.g., relative to the surgical plan or goal) such that further surgical steps are not needed.

Accordingly, in some aspects of the present technology the system 100 can intraoperatively determine spinal alignment parameters in real-time or near real-time during a spinal surgical procedure that reflect the true physical alignment of the spine within the scene. The surgeon or other user can use the determined spinal alignment parameters to track their progress through the surgical procedure and/or to confirm the effectiveness thereof. Additionally, in some embodiments the surgeon can use the determined spinal alignment parameters to guide further stages of the spinal surgical procedure. For example, if the decrease in the coronal Cobb angle was different (e.g., greater or less) than expected at the third time shown in FIG. 9C, the surgeon could change or modify a subsequent surgical step (e.g., implant size, implant location, and the like) to account for and/or to try and rectify the differences. Likewise, the system 100 can automatically analyze the determined alignment parameters to update/correct a surgical plan, as described in detail above with reference to block 538.

Some spinal surgical procedures include the introduction of rod and tower devices, and/or other surgical devices, that are used for correcting a deformity to the spine. Referring again to FIGS. 1-5 together, such surgical devices can clutter the intraoperative scene 108 and occlude anatomical structures in the scene 108, including one or more vertebrae of the spine 309. Such occlusion can reduce the accuracy of the registration of the initial image data of the spine 309 to the intraoperative image data of the spine 309. In some embodiments, the system 100 can register the initial image data to the intraoperative image data based on a known spatial relationship between one or more surgical devices in the scene 108 and the spine 309.

FIG. 10, for example, is a flow diagram of a process or method 1060 for registering initial image data to intraoperative image data (e.g., block 534 of the method 530) based on one or more surgical devices in accordance with embodiments of the present technology. Although some features of the method 1060 are described in the context of the system 100 shown in FIGS. 1-3 for the sake of illustration, one skilled in the art will readily understand that the method 1060 can be carried out using other suitable systems and/or devices described herein.

At block 1061, the method 1060 can include receiving a 3D model a surgical device configured to be secured to a vertebra of the spine 309. In some embodiments, the surgical device can be a rod and tower device configured to be rigidly affixed to the vertebra during the spinal surgical procedure. The 3D model can fully characterize/specify a shape and size of the surgical device.

At block 1062, the method 1060 can include determining a spatial relationship between the surgical device and the vertebra it is secured to. For example, the surgical device can be secured to the vertebra via one or more implants (e.g., screws) having a pose relative to the vertebra that is known from a preoperative plan and/or intraoperatively determined via the camera array 110. Based on the known relationship of the one or more implants to the vertebra and to the surgical device, the system 100 can determine (e.g., recover) the spatial relationship (e.g., rigid relationship) of the surgical device relative to the vertebra it is secured to.

At block 1063, the method 1060 can include receiving intraoperative image data of the surgical device. The intraoperative image data can include real-time or near real-time images of the surgical device in the scene 108 captured by the cameras 112 and/or the depth cameras 118. In some embodiments, the intraoperative image data includes (i) light field images from the cameras 112 and (ii) images from the depth cameras 118 that include encoded depth information about the scene 108 including the surgical device.

At block 1064, the method 1060 includes registering the initial image data of the spine 309 to the intraoperative image data based on the spatial relationship. That is, the image data of the surgical device can be used to register (e.g., align in pose and position) the initial image data to the physical spine 309 of the patient based on the rigid spatial relationship between the surgical device visible to the camera array 110 and the associated vertebra that may be occluded from the camera array 110 by the surgical device. The registration can be carried out using any of the registration methods described in detail above with reference to block 534 of the method 530 of FIG. 5. Accordingly, in some aspects of the present technology the system 100 can still determine and track alignment parameters when the spine 309 and/or other physical anatomy of the patient is occluded by surgical devices, such as rod and tower devices. In some embodiments, the method 1060 can be used to register multiple vertebrae each having a surgical device affixed thereto.

As described above with reference to block 534, some spinal deformities can be large enough that they are not entirely visible to the cameras 112 within the scene 108. In some aspects of the present technology, the system 100 can move the camera array 110 (e.g., via the arm 222) relative to the spine 309 to capture image data of the full extent of the deformity. However, some spinal surgical workflows may require that the camera array 110 remain in a fixed position relative to the scene 108 such that intraoperative image data of a portion of the spine 309 will be unavailable during some or all of the surgical procedure—thereby potentially reducing the accuracy of the registration of the initial image data of the spine 309 to the intraoperative image data of the spine 309. In some embodiments, the system 100 can register the initial image data to the intraoperative image data by tracking (e.g., optically tracking) a marker affixed to one or more vertebrae that are not visible to the camera array 110 during the procedure.

Figure 11:
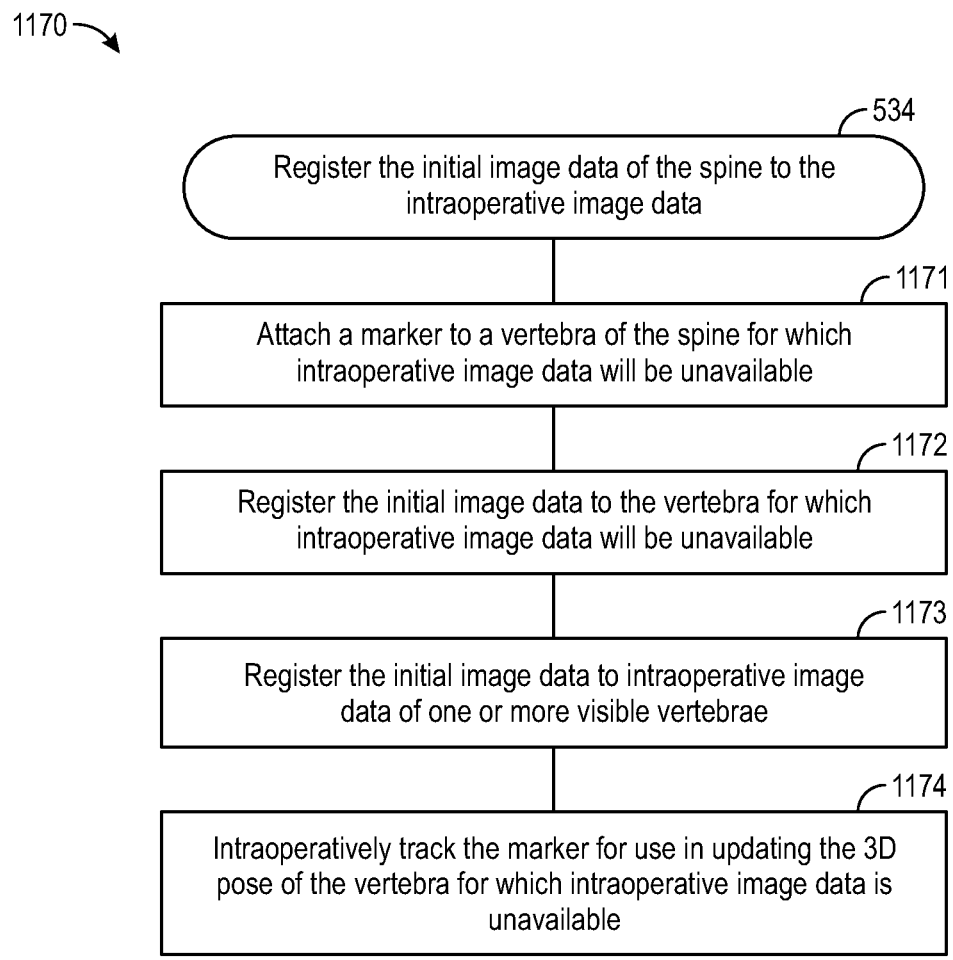
FIG. 11 is a flow diagram of a process or method for registering initial image data to intraoperative image data by tracking a marker affixed to one or more vertebrae of the spine in accordance with embodiments of the present technology.

FIG. 11, for example, is a flow diagram of a process or method 1170 for registering initial image data to intraoperative image data (e.g., block 534 of the method 530) by tracking a marker affixed to one or more vertebrae of the spine 309 in accordance with embodiments of the present technology. Although some features of the method 1170 are described in the context of the system 100 shown in FIGS. 1-3 for the sake of illustration, one skilled in the art will readily understand that the method 1170 can be carried out using other suitable systems and/or devices described herein.

At block 1171, the method 1170 can include attaching a marker to a vertebra of the spine 309 for which intraoperative image data will be unavailable during a surgical procedure. In some embodiments, the vertebra is the upper end vertebra (e.g., C7 vertebra). The marker can be an optical marker, such as a constellation of marker balls, that can be rigidly attached to the vertebra for which intraoperative image data will be unavailable. In some embodiments, the marker can have features generally similar or identical to any of the markers disclosed in U.S. patent application Ser. No. 16/749,963, titled "ALIGNING PREOPERATIVE SCAN IMAGES TO REAL-TIME OPERATIVE IMAGES FOR A MEDIATED-REALITY VIEW OF A SURGICAL SITE," filed Jan. 22, 2020, which is incorporated herein by reference in its entirety. In some embodiments, the marker is attached after surgically exposing the spine 309 but before performing corrective adjustments to the spine 309. In some embodiments, the marker is affixed to a vertebra that will not be surgically exposed during the surgical procedure and thus not visible to the camera array 110. For example, the marker can be clasped, stuck, or otherwise affixed to the skin of the patient above the vertebra. The vertebra can be a vertebra at one extreme of a curve to be measured. Referring to FIGS. 7A and 7B together, for example, to track the angle A during the surgical procedure when the vertebra for which intraoperative image data will be unavailable is the sixth vertebra 740*f*, the marker can be attached to the sixth vertebra 740*f*.

At block 1172, the method 1170 can include registering the initial image data to the vertebra for which the intraoperative image data will be/is unavailable. The initial image data can be registered/aligned to the vertebra for which intraoperative image data is unavailable based on a known pose of the marker relative to the vertebra. In some embodiments, if the vertebra for which intraoperative image data will be unavailable is not surgically exposed, the initial pose of the vertebra can be determined using another imaging modality—such as by taking a CT or fluoroscopic image of the vertebra. The system can then perform a 2D or 3D rigid registration between the captured images of the vertebra and the rigid positions of the attached marker.

At block 1173, the method 1170 can include registering the initial image data to the intraoperative image data of one or more visible vertebrae (i.e., for which intraoperative image data is available). The initial image data can be registered to the intraoperative image data of the one or more visible vertebrae using any of the registration techniques discussed in detail herein (e.g., by detecting positions of fiducial markers and/or feature points visible in both data sets).

At block 1174, the method 1170 can include intraoperatively tracking the marker for use in updating the pose of a 3D characterization of the vertebra for which intraoperative image data is unavailable. The system 100 can track the marker via the trackers 113 or, if the marker is not within the field of view of the trackers 113, via an auxiliary tracking unit. In some embodiments, the system 100 tracks the marker via optical tracking, radiofrequency identification (RFID) tracking, electromagnetic tracking, and/or the like. Accordingly, by tracking (via the marker) the vertebra for which intraoperative image data is unavailable, the system 100 can update the pose of the vertebra thereby allowing for the determination of alignment parameters of the spine 309 (block 536) based on the vertebra for which intraoperative image data is unavailable. In some embodiments, rather than tracking the marker itself, the system 100 can track a rod (e.g., an extension rod) or other reference device coupled to the marker and that is visible to the camera array 110 during the surgical procedure (e.g., via imaging from the cameras 112 and/or the trackers 113).

In some embodiments, intraoperative image data is unavailable for more than one vertebra. For example, referring to FIGS. 7A and 7B together, intraoperative image data may be unavailable for the fourth through sixth vertebrae 740*d*—f. To recover the poses of the vertebrae 740*d-f*, a marker can be attached to each of the vertebrae 740*d-f* and used to track the vertebrae 740*d-f*. Alternatively, a marker can be attached only to the sixth vertebra 740*f*, and the system 100 can interpolate the poses of the fourth and fifth vertebra 740*d-e* based on the known and tracked pose of the sixth vertebra 740*f* (via tracking of the marker attached thereto) and the known poses of the first through third vertebrae 740*a-c* (via intraoperative image data captured thereof). Accordingly, in this manner, the system 100 can calculate alignment parameters between any two or more the vertebrae 740.

Figure 12:
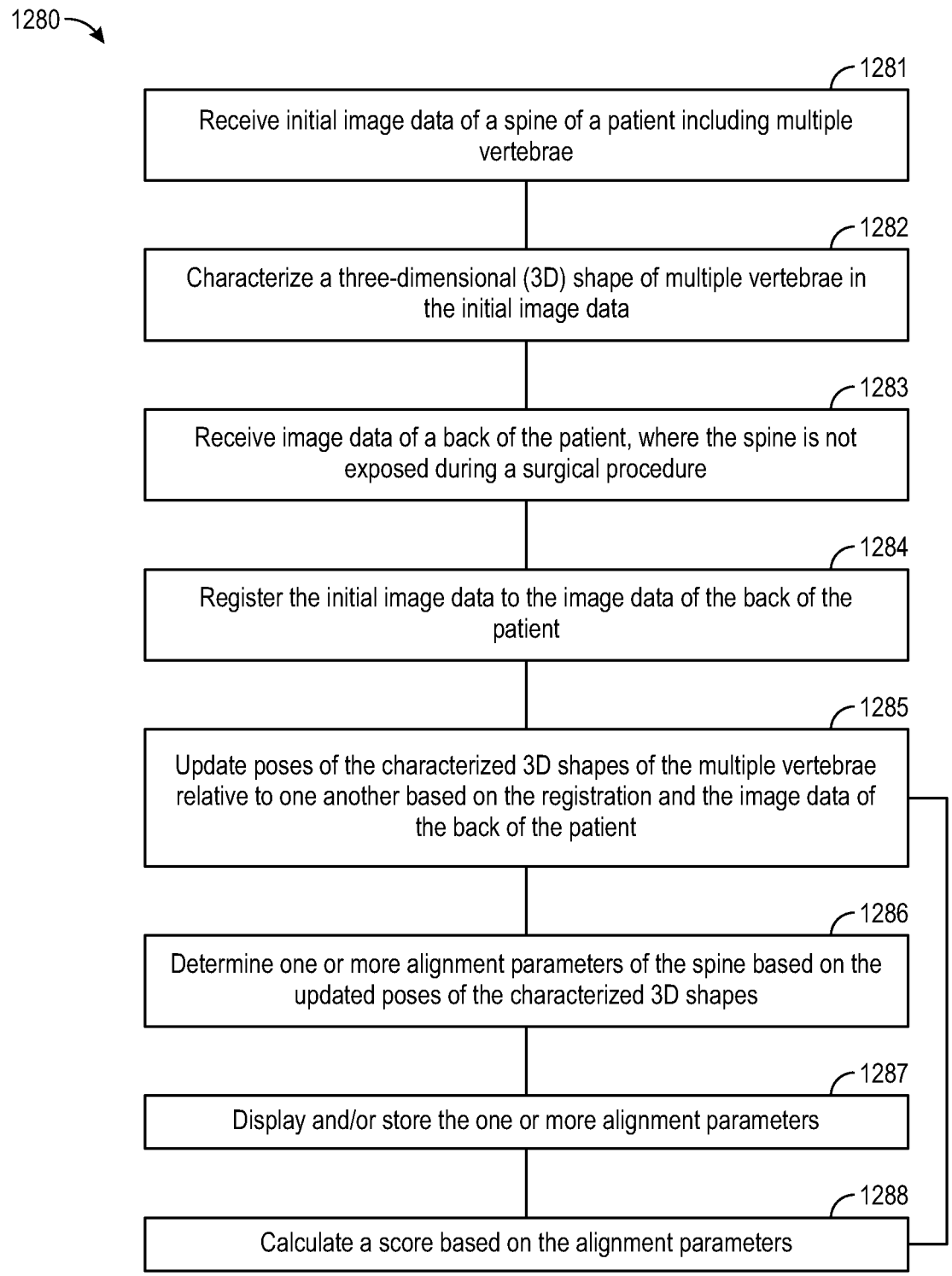
FIG. 12 is a flow diagram of a process or method for non-invasively determining alignment parameters of a spine of a patient in accordance with embodiments of the present technology.

In some embodiments, the system 100 can be used to non-invasively track and calculate alignment parameters of a spine of a patient preoperatively, postoperatively, and/or diagnostically without the spine being surgically exposed. FIG. 12, for example, is a flow diagram of a process or method 1280 for non-invasively determining alignment parameters of a spine of a patient in accordance with embodiments of the present technology. Although some features of the method 1280 are described in the context of the system 100 shown in FIGS. 1-3 for the sake of illustration, one skilled in the art will readily understand that the method 1280 can be carried out using other suitable systems and/or devices described herein.

The method 1280 can include several processing steps generally similar or identical to those of the method 530 described in detail above with reference to FIG. 5. For example, blocks 1281 and 1282 of the method 1280 can be generally identical to blocks 531 and 532, respectively, of the method 530 and include receiving initial image data of a spine of a patient and characterizing a 3D shape of multiple vertebrae in the initial image data.

At block 1283, the method 1280 can include receiving image data of a back of the patient from the camera array 110. The image data can include real-time or near-real-time images of the back captured by the cameras 112 and/or the depth cameras 118. In some embodiments, the image data includes (i) light field images from the cameras 112 and (ii) images from the depth cameras 118 that include encoded depth information about the back of the patient. In some embodiments, receiving the image data can include capturing images of the back of the patient from different viewpoints by, for example, moving (e.g., scanning) the camera array 110 relative to the back of the patient.

At block 1284, the method 1280 can include registering the initial image data to captured image data of the back of the patient to, for example, establish a transform/mapping/transformation between the captured image data and the initial image data such that these data sets can be represented in the same coordinate system. In some embodiments, the registration process includes analyzing the captured image data to identify points/regions of the spine of the patient that are visible as bumps in the skin along the back of the patient. Those points/regions can then be matched to corresponding points/regions in the initial image data.

At block 1285, the method 1280 can include updating a pose (e.g., a position and/or orientation) of each of the characterized 3D shapes of the multiple vertebrae relative to one another based on the registration and the captured image data of the back of the patient. For example, the poses of any or all of the geometric features of the vertebrae (e.g., the planes of symmetry 641, the superior endplates 642, the inferior endplates 643, the local coordinate frames, the lines 646a-b, the lines 647a-b, etc., shown in FIG. 6) can be updated relative to one another based on the registration and the currently captured image data that reflects the current physical position and alignment of the spine of the patient. Accordingly, after updating, the geometric features are aligned relative to one another such that measurements between the geometric features reflect the physical geometry of the spine of the patient—even as the spine is not exposed.

Blocks 1286-1288 of the method 1280 can be generally identical to blocks 536, 537, and 539, respectively, of the method 530. In some aspects of the present technology, by registering the spine of the patient to the initial image data when the spine is not surgically exposed allows the method 1280 to determine alignment parameters preoperatively, postoperatively, and/or diagnostically. For example, the method 1280 can detect how the alignment of the spine changes as the patient moves (e.g., on a table or while standing). Moreover, the method 1280 can determine the alignment parameters without exposing the patient to additional radiation, such as is required by many other imaging modalities (e.g., CT, MRI, X-ray).

Although reference is primarily made herein to determining alignment parameters of a spine of a patient, in other embodiments any of the systems or methods described herein (e.g., the methods 530, 1060, 1170, and/or 1280) can be carried out to determine alignment parameters for other types of surgical/anatomical targets of a patient preoperatively, intraoperatively, postoperatively, and/or diagnostically. More specifically, the methods and systems of the present technology can be used to calculate and track the alignment between different boney structures, cartilage, prosthetic implants, ligaments, etc., during a related surgical procedure.

For example, during total hip arthroplasty (THA) major measurements for cup placement include anteversion and inclination angles. Typically, there are acceptable ranges for the anteversion and inclination angles that have been shown to result in fewer dislocations. The methods and systems of the present technology can track a prosthetic implant and the anatomy of the patient to compute the anteversion and inclination angles in real-time or near real-time. Likewise, parameters for the femoral component (e.g., stem) can be calculated and, in combination with other alignment parameters, used to calculate limb length and/or other measures.

For example, the methods and systems of the present technology can be used to track portions of bone (e.g., bone fragments) and/or cartilage during a hip osteotomy or surgical hip repair for trauma, and to thereby calculate alignment parameters (e.g., biomechanical indicators) such as: lateral center edge angle, anterior center edge angle, Tonnis angle, joint contact pressure, and the like. Specifically, the system 100 can intraoperatively register bone fragments to a previously acquired model of the hip to calculate the alignment parameters. In some aspects of the present technology, such tracking and alignment parameter calculation can be done without affixing optical tracking markers (e.g., dynamic-reference-frame markers) or the like to the bone fragments for tracking—which can be difficult and cumbersome to achieve.

For example, the methods and systems of the present technology can be used to track portions of bone exposed during a craniofacial procedure, such as Le Fort osteotomies, to calculate alignment parameters related to functional goals (e.g., a patient's ability to chew) and/or aesthetics.

For example, the methods and systems of the present technology can be used to calculate alignment parameters during knee arthroplasty or other joint arthroplasties. Knee arthroplasty includes aligning the femur and tibia along the mechanical axis of the leg (e.g., from the hip joint through the middle of the knee down to the ankle) and placing multiple implants correctly on the knee in the correct orientation to create the appropriate mechanical axis. The methods and systems of the present technology can track portions of bone of the femur, tibia, etc., to calculate the mechanical axis, the alignment of the femur and tibia, and so on.

For example, the methods and systems of the present technology can be used to calculate alignment parameters during angular osteotomies (e.g., bone resections) that impact the alignment of a bone. For example, wedge osteotomies allow surgeons to change the alignment of the bone from one position to another, and the present technology can track the change in real-time or near real-time as well as help plan the actual osteotomy wedge needed to make the change.

III. ADDITIONAL EXAMPLES

The following examples are illustrative of several embodiments of the present technology:

1. A method of intraoperatively determining an alignment parameter of a spine during a surgical procedure on the spine, the method comprising:
    receiving initial image data of the spine including multiple vertebrae;

identifying a geometric feature associated with each vertebra in the initial image data, wherein the geometric features each have a pose in the initial image data;
receiving intraoperative image data of the spine;
registering the initial image data to the intraoperative image data;
updating the pose of each geometric feature based on the registration and the intraoperative image data; and
determining the alignment parameter of the spine based on the updated poses of the geometric features associated with two or more of the vertebrae.

2. The method of example 1 wherein the alignment parameter is an angle indicating a curvature of the spine.

3. The method of example 1 or example 2 wherein the alignment parameter is a Cobb angle indicating a curvature of the spine.

4. The method of any one of example 1 or example 2 wherein the alignment parameter is at least one of a Cobb angle, a lumbar lordosis measurement, a thoracic kyphosis measurement, a cervical lordosis measurement, a sagittal vertical axis, a pelvic tilt, a pelvic angle, a sacral slope, a pelvic incidence, a vertebral rotation angle, a segmental lordosis/kyphosis measurement, an anterior disc height, a posterior disc height, a foraminal height, a foraminal area, a disc volume, a spondylolisthesis grading, a vertebral body height measurement, a C7 plumbline, a center sacral vertical line, a lateral olisthesis grading, a sagittal vertical axis, a T1 tilt, a T1 pelvic angle, an L1 tilt, and an L1 pelvic angle.

5. The method of any one of examples 1-4 wherein the alignment parameter is a three-dimensional (3D) scoliotic parameter.

6. The method of any one of examples 1-5 wherein the geometric feature associated with each vertebra is an endplate.

7. The method of any one of examples 1-5 wherein the geometric feature associated with each vertebra is at least one of a plane of symmetry, a superior endplate, an inferior endplate, a vertebra-specific coordinate plane, and a line.

8. The method of any one of examples 1-7 wherein the initial image data is preoperative three-dimensional (3D) image data.

9. The method of any one of examples 1-8 wherein determining the alignment parameter of the spine includes continuously determining the alignment parameter in substantially real-time.

10. The method of any one of examples 1-9 wherein the method further comprises at least one of displaying the alignment parameter on a display and updating a surgical plan based on the determined alignment parameter.

11. The method of any one of examples 1-10 wherein the method further comprises calculating a score based on the determined alignment parameter.

12. An imaging system, comprising:
a camera array including a plurality of cameras configured to capture intraoperative image data of a spine of a patient undergoing a spinal surgical procedure; and
a processing device communicatively coupled to the camera array, wherein the processing device is configured to—
receive initial image data of the spine including multiple vertebrae;
identify a geometric feature associated with each vertebra in the initial image data, wherein the geometric features each have a pose in the initial image data;
receive the intraoperative image data of the spine from the camera array;
register the initial image data to the intraoperative image data;
update the pose of each geometric feature based on the registration and the intraoperative image data; and
determine an alignment parameter of the spine based on the updated poses of the geometric features associated with two or more of the vertebrae.

13. The imaging system of example 12 wherein the alignment parameter characterizes a curvature of the spine.

14. The imaging system of example 12 or example 13 wherein the geometric feature associated with each vertebra is an endplate, and wherein the alignment parameter is a Cobb angle.

15. The imaging system of any one of examples 12-14 wherein the processing device is configured to continuously determine the alignment parameter in substantially real time.

16. The imaging system of any one of examples 12-15, further comprising a display device, wherein the processing device is configured to display the intraoperative image data and the alignment parameter on the display device.

17. A method of determining an alignment parameter of an anatomical target of a patient, the method comprising:
receiving three-dimensional (3D) initial image data of the anatomical target including multiple portions;
identifying a geometric feature associated with each portion of the anatomical target in the initial image data, wherein the geometric feature characterizes a 3D shape of the associated portion of the anatomical target, and wherein the geometric features each have a pose relative to one another;
receiving light field image data of the anatomical target;
registering the 3D initial image data to the light field image data;
updating the pose of each geometric feature based on the registration and the light field image data; and
determining the alignment parameter of the anatomical target based on the updated poses of the geometric features associated with two or more of the portions of the anatomical target.

18. The method of example 17 wherein the anatomical target is a spine.

19. The method of example 17 or example 18 wherein the anatomical target is a boney structure.

20. The method of any one of examples 17-19 wherein determining the alignment parameter of the anatomical target includes continuously determining the alignment parameter in substantially real-time.

21. A method of intraoperatively determining an alignment parameter of a spine during a surgical procedure on the spine, the method comprising:
receiving preoperative image data of the spine including multiple vertebrae;
identifying a geometric feature associated with each vertebra in the preoperative image data, wherein the geometric features each have a pose in the preoperative image data;
receiving intraoperative image data of the spine;

registering the preoperative image data to the intraoperative image data;
updating the pose of each geometric feature based on the registration and the intraoperative image data; and
determining the alignment parameter of the spine based on the updated poses of the geometric features associated with two or more of the vertebrae.
22. The method of example 21 wherein the alignment parameter is an angle indicating a curvature of the spine.
23. The method of example 21 or example 22 wherein the alignment parameter is a Cobb angle indicating a curvature of the spine.
24. The method of example 21 or example 22 wherein the alignment parameter is at least one of a Cobb angle, a lumbar lordosis measurement, a thoracic kyphosis measurement, a cervical lordosis measurement, a sagittal vertical axis, a pelvic tilt, a pelvic angle, a sacral slope, a pelvic incidence, a vertebral rotation angle, a segmental lordosis/kyphosis measurement, an anterior disc height, a posterior disc height, a foraminal height, a foraminal area, a disc volume, a spondylolisthesis grading, a vertebral body height measurement, a C7 plumbline, a center sacral vertical line, a lateral olisthesis grading, a sagittal vertical axis, a T1 tilt, a T1 pelvic angle, an L1 tilt, and an L1 pelvic angle.
25. The method of any one of examples 21-24 wherein the alignment parameter is a three-dimensional (3D) scoliotic parameter.
26. The method of any one of examples 21-25 wherein the geometric feature associated with each vertebra is an endplate.
27. The method of any one of examples 21-25 wherein the geometric feature associated with each vertebra is at least one of a plane of symmetry, a superior endplate, an inferior endplate, a vertebra-specific coordinate plane, and a line.
28. The method of any one of examples 21-27 wherein the preoperative image data is three-dimensional (3D) computed tomography (CT) data.
29. The method of any one of examples 21-28 wherein determining the alignment parameter of the spine includes continuously determining the alignment parameter in substantially real-time.
30. The method of any one of examples 21-29 wherein the method further comprises displaying the alignment parameter on a display.
31. The method of any one of examples 21-30 wherein the method further comprises updating a surgical plan based on the determined alignment parameter.
32. An imaging system, comprising:
a camera array including a plurality of cameras configured to capture intraoperative image data of a spine of a patient undergoing a spinal surgical procedure; and
a processing device communicatively coupled to the camera array, wherein the processing device is configured to—
  receive preoperative image data of the spine including multiple vertebrae;
  identify a geometric feature associated with each vertebra in the preoperative image data, wherein the geometric features each have a pose in the preoperative image data;
  receive the intraoperative image data of the spine from the camera array;
  register the preoperative image data to the intraoperative image data;
  update the pose of each geometric feature based on the registration and the intraoperative image data; and
  determine an alignment parameter of the spine based on the updated poses of the geometric features associated with two or more of the vertebrae.
33. The imaging system of example 32 wherein the alignment parameter characterizes a curvature of the spine.
34. The imaging system of example 32 or example 33 wherein the geometric feature associated with each vertebra is an endplate, and wherein the alignment parameter is a Cobb angle.
35. The imaging system of any one of examples 32-34 wherein the processing device is configured to continuously determine the alignment parameter in substantially real-time.
36. The imaging system of any one of examples 32-34, further comprising a display device, wherein the processing device is configured to display the intraoperative image data and the alignment parameter on the display device.
37. A method of intraoperatively determining an alignment parameter of a spine during a surgical procedure on the spine, the method comprising:
receiving three-dimensional (3D) preoperative image data of the spine including multiple vertebrae;
identifying a geometric feature associated with each vertebra in the preoperative image data, wherein the geometric feature characterizes a 3D shape of the associated vertebra, and wherein the geometric features each have a pose relative to one another;
receiving intraoperative light field image data of the spine;
registering the 3D preoperative image data to the intraoperative light field image data;
updating the pose of each geometric feature based on the registration and the intraoperative light field image data; and
determining the alignment parameter of the spine based on the updated poses of the geometric features associated with two or more of the vertebrae.
38. The method of example 37 wherein the alignment parameter characterizes a curvature of the spine.
39. The method of example 37 or example 38 wherein the alignment parameter is a three-dimensional (3D) scoliotic parameter.
40. The method of any one of examples 37-39 wherein determining the alignment parameter of the spine includes continuously determining the alignment parameter in substantially real-time.
41. A method of determining an alignment parameter of an anatomical target, the method comprising:
receiving initial image data of the anatomical target including multiple portions;
identifying a geometric feature associated with each portion of the anatomical target in the initial image data, wherein the geometric features each have a pose in the initial image data;
receiving current image data of the anatomical target;
registering the initial image data to the current image data;
updating the pose of each geometric feature based on the registration and the current image data; and
determining the alignment parameter of the anatomical feature based on the updated poses of the geometric features associated with two or more of the portions of the anatomical target.

42. The method of example 41 wherein the alignment parameter is an angle indicating a curvature of the anatomical target.

43. The method of any one of example 41 or example 42 wherein the alignment parameter is a three-dimensional (3D) parameter.

44. The method of any one of examples 41-43 wherein the geometric feature associated with each portion of the anatomical target is an endplate.

45. The method of any one of examples 41-43 wherein the geometric feature associated with each portion of the anatomical target is at least one of a plane of symmetry, a superior endplate, an inferior endplate, a vertebra-specific coordinate plane, and a line.

46. The method of any one of examples 41-45 wherein the initial image data is preoperative three-dimensional (3D) image data.

47. The method of any one of examples 41-46 wherein determining the alignment parameter of the anatomical target includes continuously determining the alignment parameter in substantially real-time.

48. The method of any one of examples 41-47 wherein the method further comprises at least one of displaying the alignment parameter on a display and updating a surgical plan based on the determined alignment parameter.

49. The method of any one of examples 41-48 wherein the method further comprises calculating a score based on the determined alignment parameter.

50. An imaging system, comprising:
a camera array including a plurality of cameras configured to capture current image data of an anatomical target a patient; and
a processing device communicatively coupled to the camera array, wherein the processing device is configured to—
  receive initial image data of the anatomical target including multiple portions;
  identify a geometric feature associated with each portion of the anatomical target in the initial image data, wherein the geometric features each have a pose in the initial image data;
  receive the current image data of the anatomical target from the camera array;
  register the initial image data to the current image data;
  update the pose of each geometric feature based on the registration and the current image data; and
  determine an alignment parameter of the anatomical target based on the updated poses of the geometric features associated with two or more of the portions of the anatomical target.

51. The imaging system of example 50 wherein the alignment parameter characterizes a curvature of the anatomical target.

52. The imaging system of example 50 or example 51 wherein the geometric feature associated with each portion of the anatomical target is an endplate, and wherein the alignment parameter is an angle.

53. The imaging system of any one of examples 50-52 wherein the processing device is configured to continuously determine the alignment parameter in substantially real time.

54. The imaging system of any one of examples 50-53, further comprising a display device, wherein the processing device is configured to display the current image data and the alignment parameter on the display device.

IV. CONCLUSION

The above detailed description of embodiments of the technology are not intended to be exhaustive or to limit the technology to the precise form disclosed above. Although specific embodiments of, and examples for, the technology are described above for illustrative purposes, various equivalent modifications are possible within the scope of the technology as those skilled in the relevant art will recognize. For example, although steps are presented in a given order, alternative embodiments may perform steps in a different order. The various embodiments described herein may also be combined to provide further embodiments.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with some embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A method of intraoperatively determining an alignment parameter of a spine during a surgical procedure on the spine, the method comprising:
  receiving initial image data of the spine including multiple vertebrae;
  identifying a geometric feature associated with each vertebra in the initial image data, wherein the geometric features each have a pose in the initial image data; and
  continuously, in substantially real-time—
    receiving intraoperative image data of the spine, wherein the intraoperative image data includes depth data of the spine from a depth sensor and light field image data of the spine from multiple cameras;
    registering the initial image data to the intraoperative image data based at least in part on the light field image data;
    updating the pose of each geometric feature based on the registration and the intraoperative image data; and
    determining the alignment parameter of the spine based on the updated poses of the geometric features associated with two or more of the vertebrae.

2. The method of claim 1 wherein the alignment parameter is an angle indicating a curvature of the spine.

3. The method of claim 1 wherein the alignment parameter is a Cobb angle indicating a curvature of the spine.

4. The method of claim 1 wherein the alignment parameter is at least one of a Cobb angle, a lumbar lordosis measurement, a thoracic kyphosis measurement, a cervical lordosis measurement, a sagittal vertical axis, a pelvic tilt, a pelvic angle, a sacral slope, a pelvic incidence, a vertebral rotation angle, a segmental lordosis/kyphosis measurement, an anterior disc height, a posterior disc height, a foraminal height, a foraminal area, a disc volume, a spondylolisthesis grading, a vertebral body height measurement, a C7 plumbline, a center sacral vertical line, a lateral olisthesis grading, a sagittal vertical axis, a T1 tilt, a T1 pelvic angle, an L1 tilt, and an L1 pelvic angle.

5. The method of claim 1 wherein the alignment parameter is a three-dimensional (3D) scoliotic parameter.

6. The method of claim 1 wherein the geometric feature associated with each vertebra is an endplate.

7. The method of claim 1 wherein the geometric feature associated with each vertebra is at least one of a plane of symmetry, a superior endplate, an inferior endplate, a vertebra-specific coordinate plane, and a line.

8. The method of claim 1 wherein the initial image data is three-dimensional (3D) image data.

9. The method of claim 1 wherein the method further comprises at least one of displaying the alignment parameter on a display and updating a surgical plan based on the determined alignment parameter.

10. The method of claim 1 wherein the method further comprises calculating a score based on the determined alignment parameter.

11. The method of claim 1 wherein the light field camera comprises the depth sensor.

12. The method of claim 1 wherein the light field image data comprises information about the intensity of light rays in a scene including the spine and information about a direction the light rays are traveling through the scene.

13. The method of claim 12 wherein the cameras are RGB cameras.

14. The method of claim 1 wherein the multiple cameras are rigidly fixed to a common frame, wherein the cameras each have a focal axis, and wherein the focal axes of the cameras converge.

15. An imaging system, comprising:
a camera array including a plurality of cameras configured to capture intraoperative image data of a spine of a patient undergoing a spinal surgical procedure; and
a processing device communicatively coupled to the camera array, wherein the processing device is configured to—
receive initial image data of the spine including multiple vertebrae;
identify a geometric feature associated with each vertebra in the initial image data, wherein the geometric features each have a pose in the initial image data; and
continuously in substantially real-time—
receive the intraoperative image data of the spine from the camera array, wherein the intraoperative image data includes depth data of the spine from a depth sensor and light field image data of the spine from multiple cameras;
register the initial image data to the intraoperative image data based at least in part on the light field image data;
update the pose of each geometric feature based on the registration and the intraoperative image data; and
determine an alignment parameter of the spine based on the updated poses of the geometric features associated with two or more of the vertebrae.

16. The imaging system of claim 15 wherein the alignment parameter characterizes a curvature of the spine.

17. The imaging system of claim 15 wherein the geometric feature associated with each vertebra is an endplate, and wherein the alignment parameter is a Cobb angle.

18. The imaging system of claim 15, further comprising a display device, wherein the processing device is configured to display the intraoperative image data and the alignment parameter on the display device.

19. The imaging system of claim 15 wherein the light field camera comprises the depth sensor.

* * * * *